(12) United States Patent
Lewis

(10) Patent No.: US 10,962,789 B1
(45) Date of Patent: Mar. 30, 2021

(54) DIGITAL EYEWEAR SYSTEM AND METHOD FOR THE TREATMENT AND PREVENTION OF MIGRAINES AND PHOTOPHOBIA

(71) Applicant: Percept Technologies Inc., Los Altos, CA (US)

(72) Inventor: Scott W. Lewis, Las Vegas, NV (US)

(73) Assignee: Percept Technologies Inc, Las Vegas, NV (US)

(*) Notice: Subject to any disclaimer, the term of this patent is extended or adjusted under 35 U.S.C. 154(b) by 0 days.

(21) Appl. No.: 16/939,087

(22) Filed: Jul. 27, 2020

Related U.S. Application Data

(63) Continuation of application No. 16/655,186, filed on Oct. 16, 2019, which is a continuation of application
(Continued)

(51) Int. Cl.
*G02B 27/01* (2006.01)
*G02C 11/00* (2006.01)
(Continued)

(52) U.S. Cl.
CPC .......... *G02B 27/0172* (2013.01); *A61B 3/113* (2013.01); *G02B 27/0093* (2013.01); *G02B 27/017* (2013.01); *G02C 7/00* (2013.01); *G02C 7/101* (2013.01); *G02C 7/12* (2013.01); *G02C 11/10* (2013.01); *G06F 3/011* (2013.01); *G06F 3/013* (2013.01); *G02B 5/30* (2013.01);
(Continued)

(58) Field of Classification Search
CPC ........ G02B 27/0172; G02B 2027/0178; G02B 27/0176; G02B 27/0101; G02B 2027/0118

USPC .......................................................... 359/630
See application file for complete search history.

(56) References Cited

U.S. PATENT DOCUMENTS 4,279,474 A   7/1981   Belgorod
4,300,818 A   11/1981   Schachar
(Continued)

OTHER PUBLICATIONS

Dohi, Lecture Notes in Computer Science.

*Primary Examiner* — Mohammed A Hasan

(57) ABSTRACT

Digital eyewear for monitoring, detecting, and predicting, preventing, treating, and training patients to conduct self-care, of migraines/photophobia in real-time. Digital eyewear for similar activity, with respect to negative visual effects, such as from changes in lighting conditions. Digital eyewear maintains information about progress of migraines/photophobia for each patient individually and collectively. Digital eyewear determines whether migraines/photophobia are likely or occurring. Digital eyewear ameliorates and treats migraines/photophobia. Digital eyewear trains the patient to self-care re migraines/photophobia. Digital eyewear receives information from patient and ambient sensors, maintains history of migraines/photophobia and amelioration/treatment, and determines correlations. Patient sensors receive information about patient status. Ambient sensors receive information about ambient environment near the patient. Digital eyewear presents augmented reality and sensory inputs to ameliorate/treat migraines/photophobia, and rewards improvements in self-care. Digital eyewear communicates with remotely maintained and updated data repositories and remote treatment servers, and in coordination with other instances of digital eyewear.

30 Claims, 11 Drawing Sheets

Related U.S. Application Data

No. 16/138,951, filed on Sep. 21, 2018, which is a continuation-in-part of application No. 15/942,591, filed on Apr. 2, 2018, now abandoned, which is a continuation-in-part of application No. 15/460,197, filed on Mar. 15, 2017, which is a continuation-in-part of application No. 14/589,817, filed on Jan. 5, 2015, now Pat. No. 9,658,473, which is a continuation of application No. 14/288,189, filed on May 27, 2014, now abandoned, which is a continuation of application No. 13/965,050, filed on Aug. 12, 2013, now Pat. No. 8,733,927, which is a continuation of application No. 13/841,141, filed on Mar. 15, 2013, now Pat. No. 8,696,113.

(51) Int. Cl.
| | | |
|---|---|---|
| *G06F 3/01* | (2006.01) | |
| *A61B 3/113* | (2006.01) | |
| *G02C 7/00* | (2006.01) | |
| *G02C 7/10* | (2006.01) | |
| *G02C 7/12* | (2006.01) | |
| *G02B 27/00* | (2006.01) | |
| *G02B 5/30* | (2006.01) | |

(52) U.S. Cl.
CPC ............... *G02B 2027/0127* (2013.01); *G02B 2027/0138* (2013.01); *G02B 2027/0141* (2013.01); *G02B 2027/0178* (2013.01); *G02B 2027/0187* (2013.01)

(56) References Cited

U.S. PATENT DOCUMENTS

| | | |
|---|---|---|
| 5,212,677 A | 5/1993 | Shimote et al. |
| 5,305,012 A | 4/1994 | Faris |
| 5,552,841 A | 9/1996 | Gallorini et al. |
| 5,583,795 A | 12/1996 | Smyth |
| 5,617,035 A | 4/1997 | Swapp |
| 5,751,260 A | 5/1998 | Nappi et al. |
| 5,886,822 A | 3/1999 | Spitzer |
| 6,091,378 A | 7/2000 | Richardson et al. |
| 6,099,124 A | 8/2000 | Hidaji |
| 6,106,119 A | 8/2000 | Edwards |
| 6,222,508 B1 | 4/2001 | Alvelda et al. |
| 6,231,193 B1 | 5/2001 | Dillon |
| 6,307,526 B1 | 10/2001 | Mann |
| 6,603,443 B1 | 8/2003 | Hildebrand et al. |
| 6,608,615 B1 | 8/2003 | Martins |
| 6,647,269 B2 | 11/2003 | Hendry et al. |
| 6,836,669 B2 | 12/2004 | Miyake et al. |
| 7,370,016 B1 | 5/2008 | Hunter et al. |
| 7,436,568 B1 | 10/2008 | Kuykendall, Jr. |
| 7,486,926 B2 | 2/2009 | White et al. |
| 7,538,744 B1 | 5/2009 | Liu et al. |
| 7,539,175 B2 | 5/2009 | White et al. |
| 7,561,143 B1 | 7/2009 | Milekic |
| 7,651,220 B1 | 1/2010 | Pattikonda |
| 7,677,734 B2 | 3/2010 | Wallace |
| 7,693,384 B2 | 4/2010 | Lee et al. |
| 7,738,179 B2 | 6/2010 | Nishi |
| 7,758,185 B2 | 7/2010 | Lewis |
| 7,918,556 B2 | 4/2011 | Lewis |
| 8,238,926 B2 | 8/2012 | Lewis |
| 8,275,382 B2 | 9/2012 | Lewis |
| 8,353,594 B2 | 1/2013 | Lewis |
| 8,451,850 B2 | 5/2013 | Lewis |
| 8,566,894 B2 | 10/2013 | Lewis |
| 8,594,636 B2 | 11/2013 | Lewis |
| 8,696,113 B2 | 4/2014 | Lewis |
| 8,733,927 B1 | 5/2014 | Lewis |
| 8,733,928 B1 | 5/2014 | Lewis |
| 8,830,963 B2 | 9/2014 | Lewis |
| 8,885,882 B1 | 11/2014 | Yin et al. |
| 9,010,929 B2 | 4/2015 | Lewis |
| 9,061,025 B2 | 6/2015 | Burstein et al. |
| 9,230,292 B2 | 1/2016 | Amin et al. |
| 9,235,064 B2 | 1/2016 | Lewis |
| 9,239,473 B2 | 1/2016 | Lewis |
| 9,244,293 B2 | 1/2016 | Lewis |
| 9,264,319 B2 | 2/2016 | Lewis |
| 9,323,325 B2 | 4/2016 | Perez et al. |
| 9,363,541 B2 | 6/2016 | Lewis |
| D784,362 S | 4/2017 | Amin |
| 9,658,473 B2 | 5/2017 | Lewis |
| 9,740,552 B2 | 8/2017 | Lewis |
| 9,843,897 B1 | 12/2017 | Lin et al. |
| 10,021,430 B1 | 7/2018 | Lewis |
| 10,091,084 B2 | 10/2018 | Tao et al. |
| 10,093,252 B2 | 10/2018 | Zych |
| 10,151,937 B2 | 12/2018 | Lewis |
| 2001/0029583 A1 | 10/2001 | Palatov et al. |
| 2001/0055152 A1 | 12/2001 | Richards |
| 2002/0044152 A1 | 4/2002 | Abbott, III et al. |
| 2002/0046122 A1 | 4/2002 | Barber et al. |
| 2002/0056118 A1 | 5/2002 | Hunter et al. |
| 2002/0075210 A1 | 6/2002 | Nestorovic et al. |
| 2002/0102993 A1 | 8/2002 | Hendrey et al. |
| 2002/0105482 A1 | 8/2002 | Lemelson et al. |
| 2002/0140899 A1 | 10/2002 | Blum et al. |
| 2002/0188219 A1 | 12/2002 | Suchard |
| 2003/0001981 A1 | 1/2003 | Milne |
| 2003/0071962 A1 | 4/2003 | Nishihara |
| 2003/0142041 A1 | 7/2003 | Barlow et al. |
| 2003/0161354 A1 | 8/2003 | Bader et al. |
| 2004/0108971 A1 | 7/2004 | Waldern et al. |
| 2004/0148551 A1 | 7/2004 | Kawahara |
| 2004/0156554 A1 | 8/2004 | McIntyre |
| 2005/0020910 A1 | 1/2005 | Quadling et al. |
| 2005/0049022 A1 | 3/2005 | Mullen |
| 2005/0057701 A1 | 3/2005 | Weiss |
| 2005/0175218 A1 | 8/2005 | Vertegaal et al. |
| 2005/0206583 A1 | 9/2005 | Lemelson et al. |
| 2005/0211764 A1 | 9/2005 | Barcelou |
| 2005/0246282 A1 | 11/2005 | Naslund et al. |
| 2005/0249196 A1 | 11/2005 | Ansari et al. |
| 2006/0023158 A1 | 2/2006 | Howell et al. |
| 2006/0023595 A1 | 2/2006 | Erickson et al. |
| 2006/0050232 A1 | 3/2006 | Dukes et al. |
| 2006/0075441 A1 | 4/2006 | Gauba et al. |
| 2006/0093998 A1 | 5/2006 | Vertegaal et al. |
| 2006/0132382 A1 | 6/2006 | Jannard |
| 2006/0140502 A1 | 6/2006 | Tseng et al. |
| 2006/0158639 A1 | 6/2006 | Campin et al. |
| 2006/0146275 A1 | 7/2006 | Mertz |
| 2006/0244908 A1 | 11/2006 | Cano |
| 2006/0282864 A1 | 12/2006 | Gupte |
| 2007/0002039 A1 | 1/2007 | Pendleton et al. |
| 2007/0081123 A1* | 4/2007 | Lewis ............... G09G 3/00 351/159.39 |
| 2007/0143793 A1 | 6/2007 | Barratt et al. |
| 2007/0153498 A1 | 7/2007 | Wilt et al. |
| 2007/0161972 A1 | 7/2007 | Felberg et al. |
| 2007/0226575 A1 | 9/2007 | Zhang et al. |
| 2007/0282678 A1 | 12/2007 | Dendi et al. |
| 2008/0062378 A1 | 3/2008 | McCracken |
| 2008/0186449 A1 | 8/2008 | Sur et al. |
| 2008/0316605 A1 | 12/2008 | Hazell et al. |
| 2009/0103044 A1 | 4/2009 | Duston et al. |
| 2009/0207373 A1 | 8/2009 | Stinson |
| 2009/0209723 A1 | 8/2009 | Lesartre et al. |
| 2009/0216092 A1 | 8/2009 | Waldorf et al. |
| 2009/0268162 A1 | 10/2009 | Stetson et al. |
| 2010/0002191 A1 | 1/2010 | Drobe |
| 2010/0045928 A1 | 2/2010 | Levy |
| 2010/0067335 A1 | 3/2010 | Li et al. |
| 2010/0149073 A1 | 6/2010 | Chaum et al. |
| 2010/0305411 A1 | 12/2010 | Paul |
| 2011/0007275 A1 | 1/2011 | Yoo et al. |
| 2011/0213664 A1 | 9/2011 | Osterhout et al. |
| 2012/0019662 A1 | 1/2012 | Maltz |
| 2012/0021806 A1 | 1/2012 | Maltz |

(56) References Cited

U.S. PATENT DOCUMENTS

| | | |
|---|---|---|
| 2012/0088526 A1 | 4/2012 | Linder |
| 2012/0154277 A1 | 6/2012 | Bar-Zeev et al. |
| 2012/0229248 A1 | 9/2012 | Pashionikar et al. |
| 2012/0235902 A1 | 9/2012 | Eisenhardt et al. |
| 2012/0242678 A1 | 9/2012 | Border et al. |
| 2012/0293548 A1 | 11/2012 | Perez et al. |
| 2012/0293773 A1 | 11/2012 | Publicover et al. |
| 2012/0329764 A1 | 12/2012 | Burstein et al. |
| 2013/0117377 A1 | 5/2013 | Miller |
| 2013/0156265 A1 | 6/2013 | Hennessy |
| 2013/0293844 A1 | 11/2013 | Gross et al. |
| 2014/0002796 A1 | 1/2014 | Marcos Munoz |
| 2014/0303124 A1 | 10/2014 | Burstein et al. |
| 2014/0347265 A1 | 11/2014 | Aimone et al. |
| 2018/0177976 A1 | 6/2018 | Burstein |

\* cited by examiner

Panel A
Digital Eyewear 100

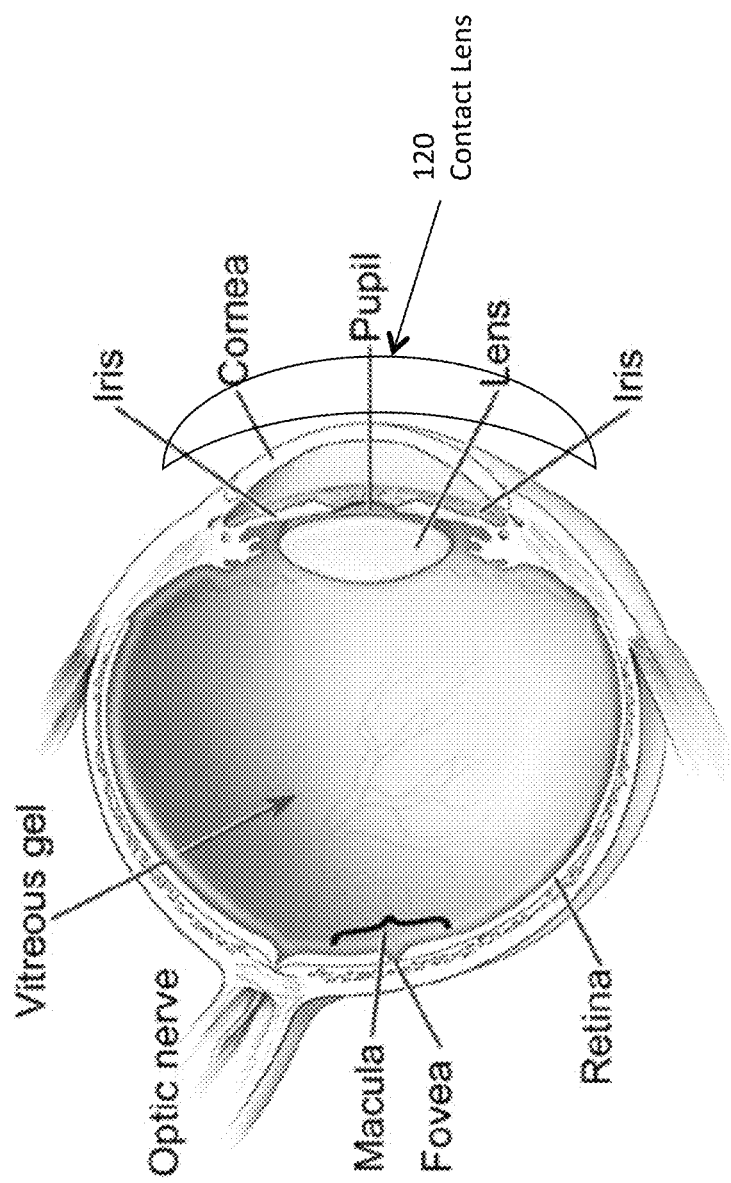

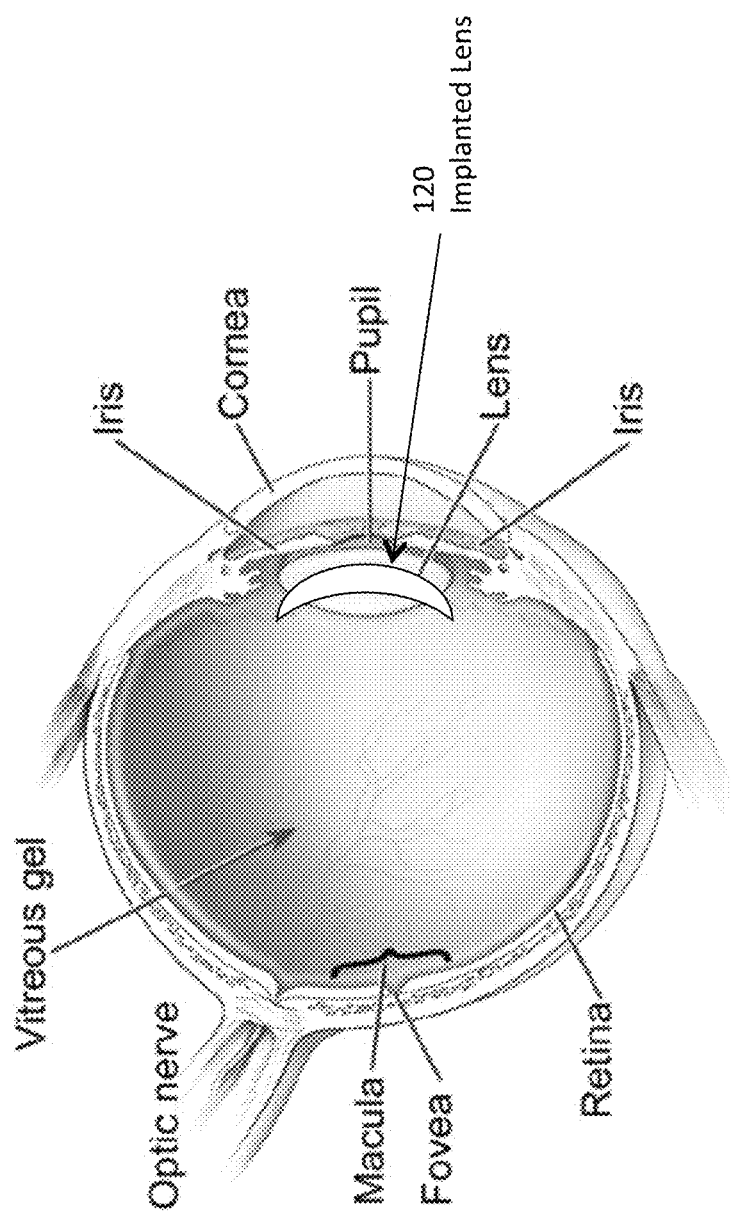

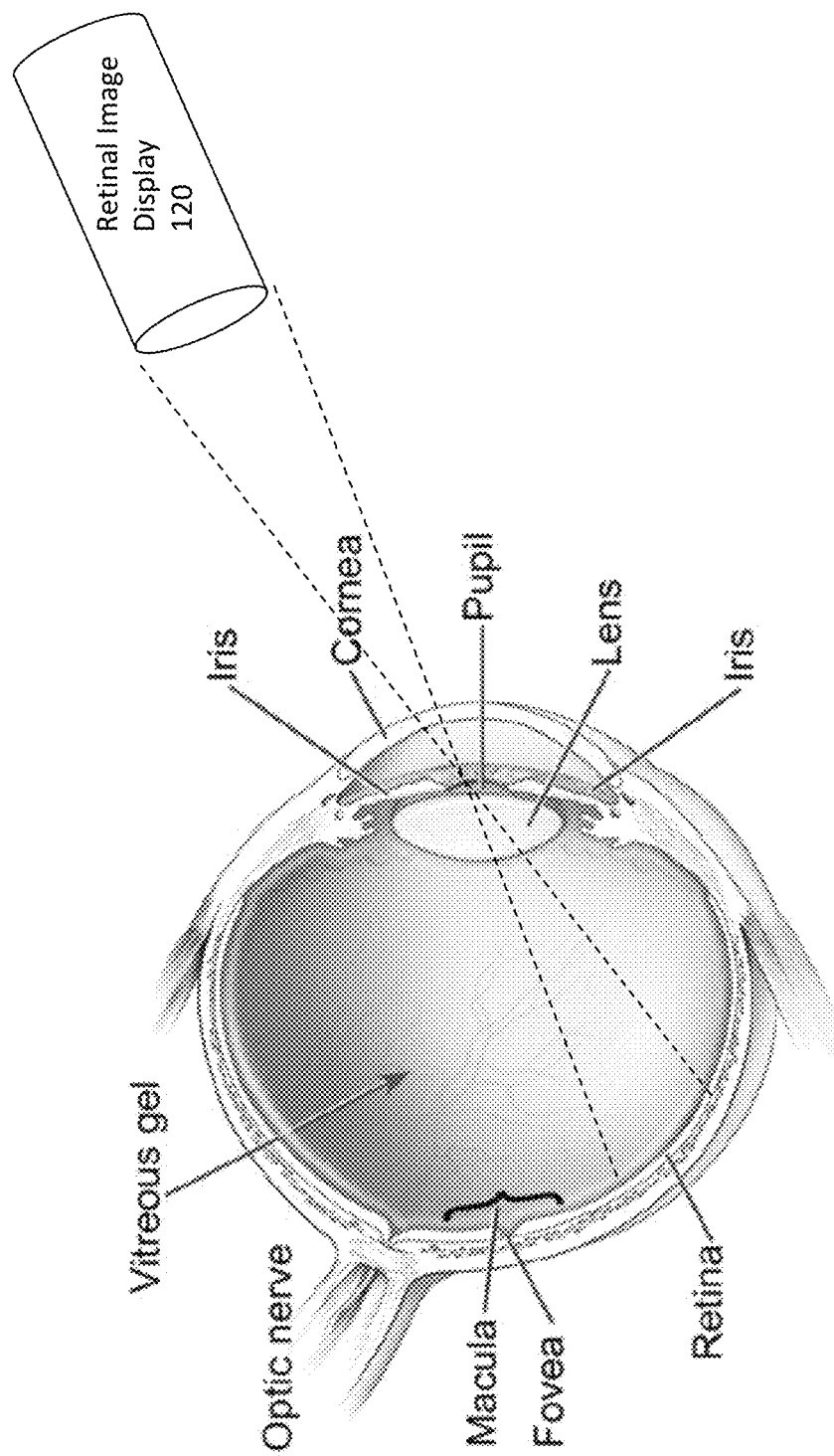

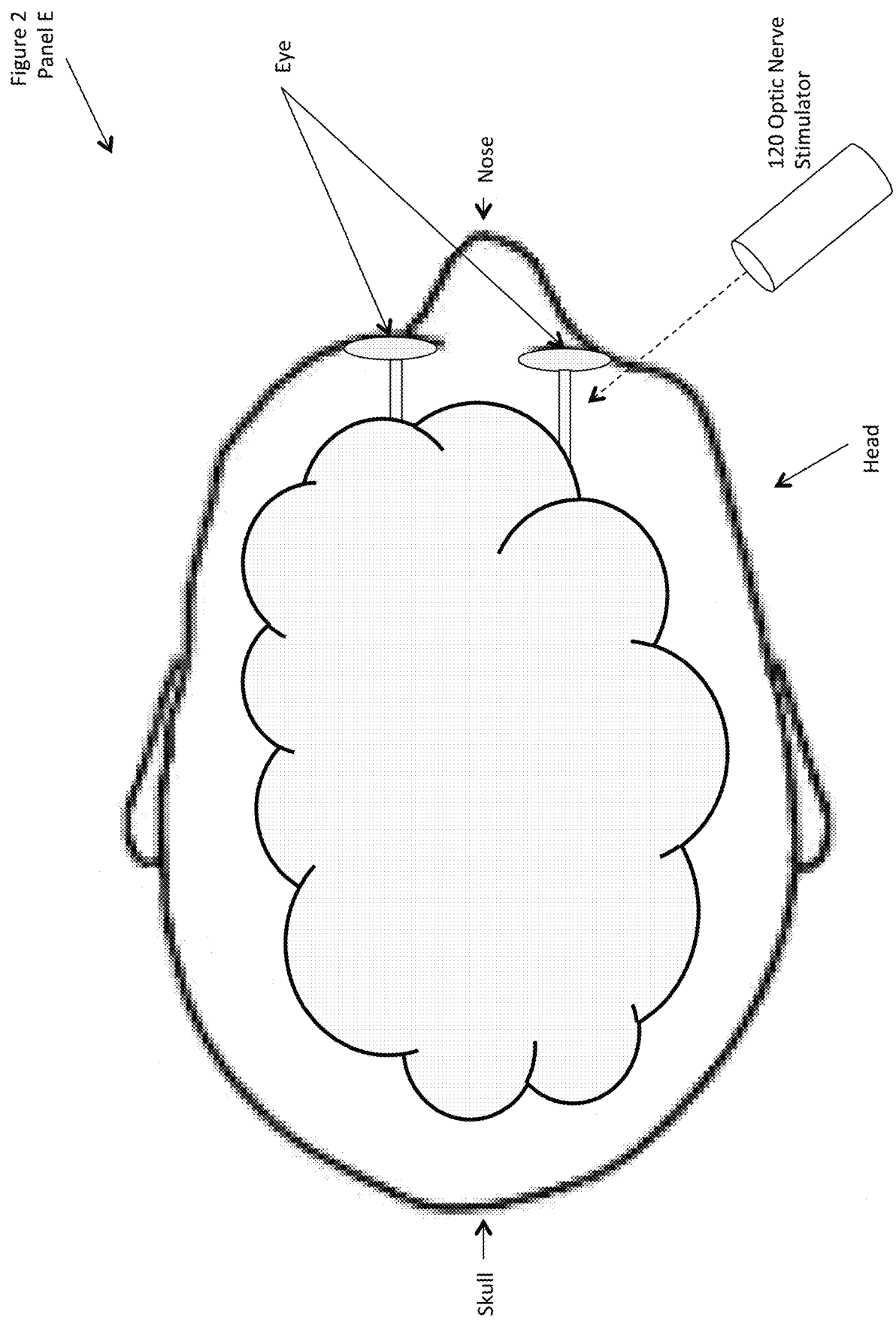

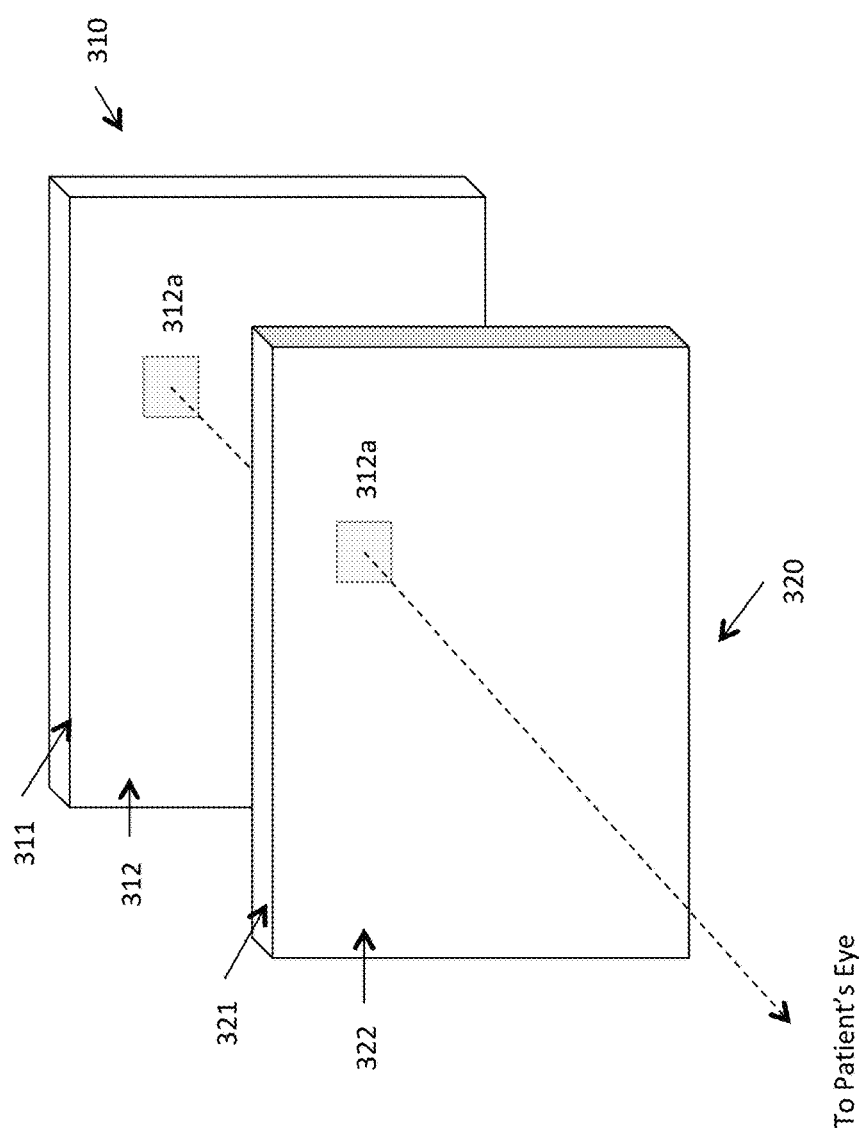

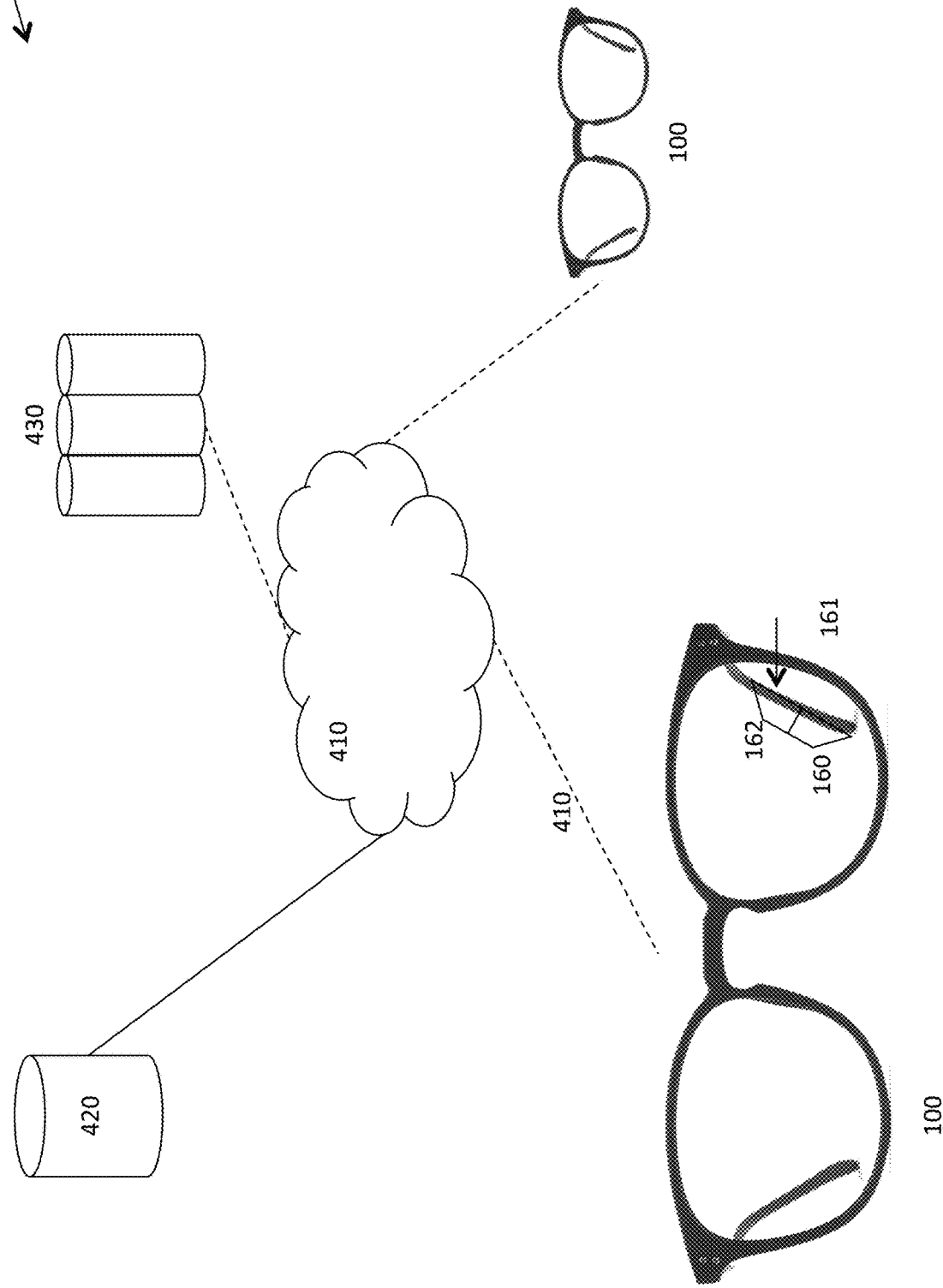

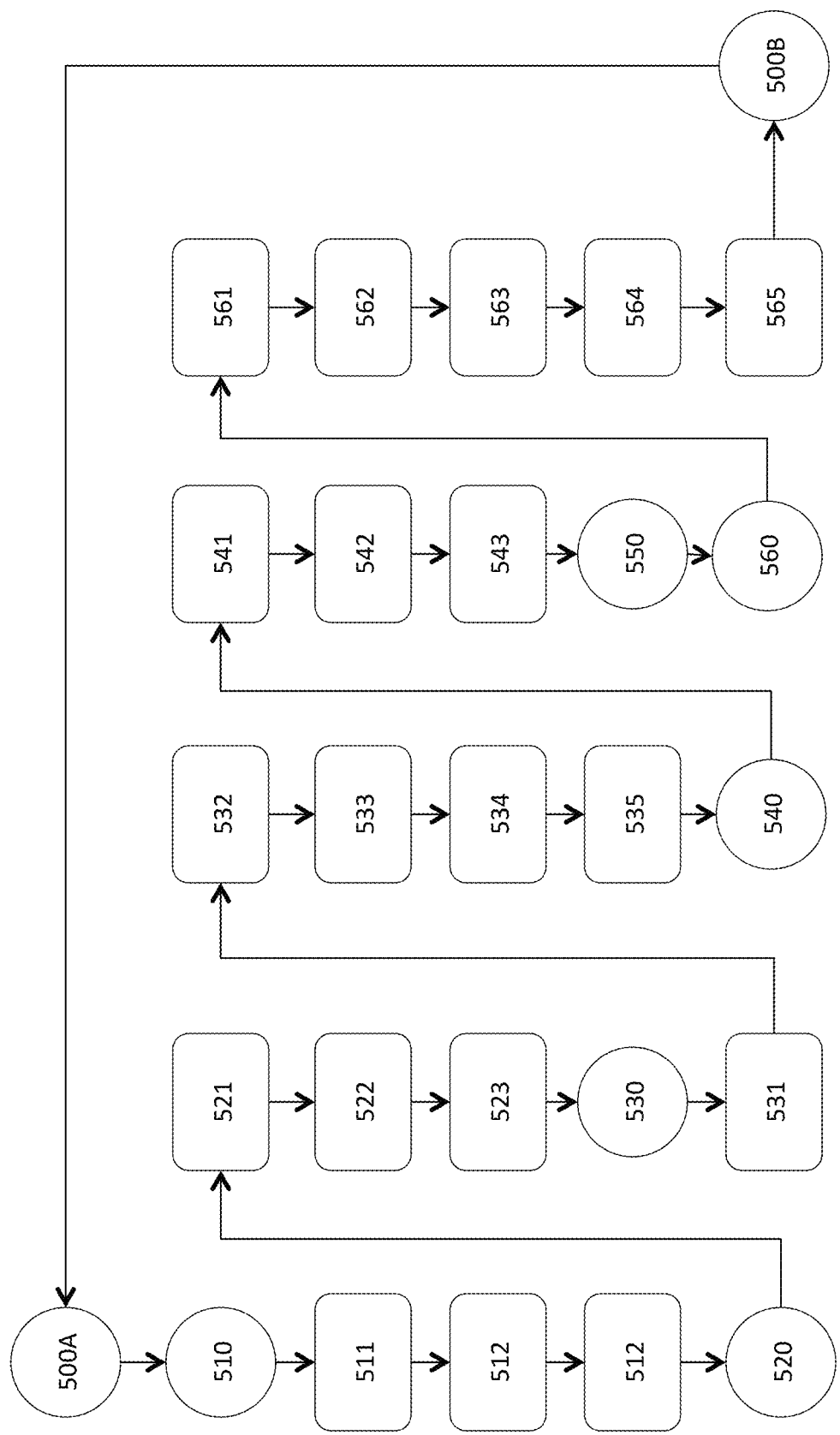
Figure 5 Method 500

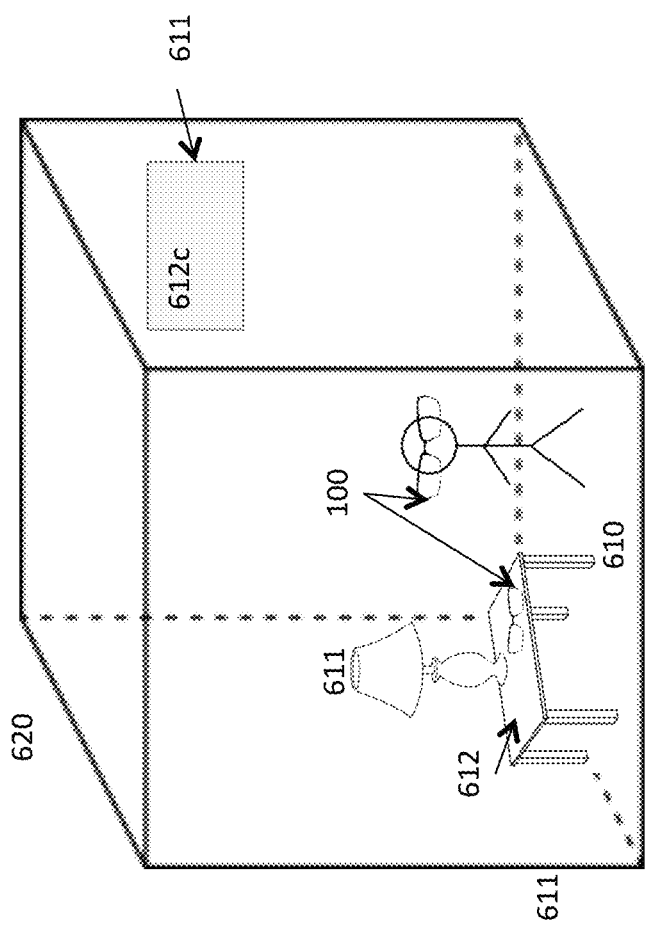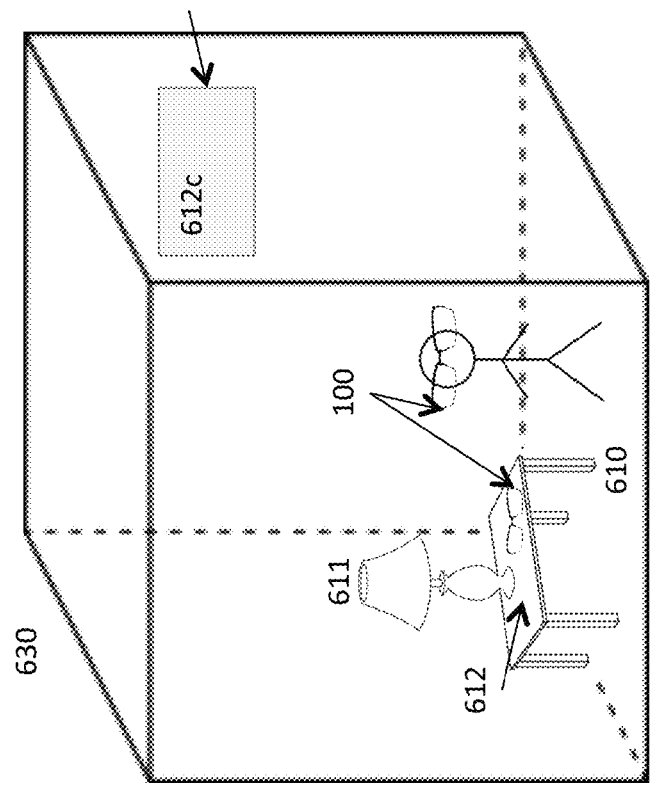

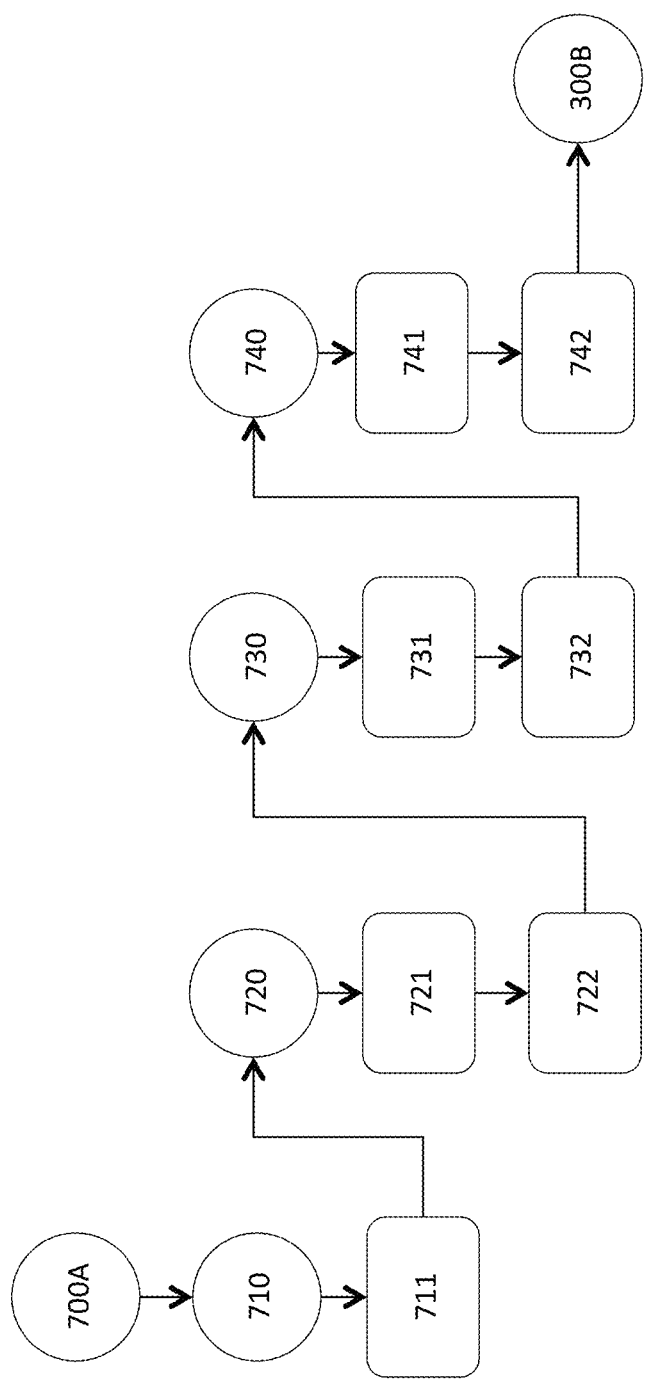

DIGITAL EYEWEAR SYSTEM AND METHOD FOR THE TREATMENT AND PREVENTION OF MIGRAINES AND PHOTOPHOBIA

PRIORITY CLAIM

This Application describes technologies that can be used with inventions, and other technologies, described in one or more of the following documents. This Application claims priority, to the fullest extent permitted by law, of these documents.

This Application is a continuation of

Application Ser. No. 16/138,941, filed Sep. 21, 2018, naming inventor Scott LEWIS, titled "Digital eyewear procedures related to dry eyes", currently pending;

which is a continuation-in-part of

Application Ser. No. 15/942,951, filed Apr. 2, 2018, naming inventor Scott LEWIS, titled "Digital Eyewear System and Method for the Treatment and Prevention of Migraines and Photophobia", currently pending;

which is a continuation-in-part of

Application Ser. No. 15/460,197, filed Mar. 15, 2017, naming inventor Scott LEWIS, titled "Digital Eyewear Augmenting Wearer's Interaction with their Environment", unpublished, currently pending;

which is a continuation-in-part of

Application Ser. No. 14/589,817, filed Jan. 5, 2015, naming inventor Scott LEWIS, titled "Enhanced Optical and Perceptual Digital Eyewear", now issued as U.S. Pat. No. 9,658,473;

which is a continuation of

Application Ser. No. 14/288,189, filed May 27, 2014, naming inventor Scott LEWIS, titled "Enhanced Optical and Perceptual Digital Eye-wear", now abandoned;

which is a continuation of

Application Ser. No. 13/965,050, filed Aug. 12, 2013, naming inventor Scott LEWIS, titled "Enhanced Optical and Perceptual Digital Eye-wear", now issued as U.S. Pat. No. 8,733,927;

which is a continuation of

Application Ser. No. 13/841,141, filed Mar. 15, 2013, naming inventor Scott LEWIS, titled "Enhanced Optical and Perceptual Digital Eye-wear", now issued as U.S. Pat. No. 8,696,113.

Each of these documents is hereby incorporated by reference as if fully set forth herein. Techniques described in this Application can be elaborated with detail found therein. These documents are sometimes referred to herein as the "Incorporated Disclosures," the "Incorporated Documents," or variants thereof.

OTHER DOCUMENTS

This Application describes technologies that can be used with inventions, and other technologies, described in one or more of the following documents. These documents are sometimes referred to herein as the "Incorporated Disclosures," the "Incorporated Documents," or variants thereof. Each and every one of these documents, as well as all documents cited therein, are hereby incorporated by reference as if fully recited herein.

US 2013/0242262 A1, filed Mar. 15, 2013, in the name of inventor Scott LEWIS, titled "Enhanced Optical and Perceptual Digital Eyewear", published Sep. 19, 2013, and all documents which that document incorporates by reference, and all applications from which that document claims priority.

U.S. Pat. No. 8,733,927 B1, filed Aug. 12, 2013, in the name of inventor Scott LEWIS, titled "Enhanced Optical and Perceptual Digital Eyewear", application Ser. No. 13/965,050, and all documents which that document incorporates by reference, and all applications from which that document claims priority.

U.S. Pat. No. 8,733,928 B1, filed Aug. 12, 2013, in the name of inventor Scott LEWIS, titled "Enhanced Optical and Perceptual Digital Eyewear", application Ser. No. 13/965,065, and all documents which that document incorporates by reference, and all applications from which that document claims priority.

U.S. application Ser. No. 15/460,197, filed Mar. 15, 2017, in the name of inventor Scott LEWIS, titled "Digital Eyewear Augmenting Wearer's Interaction with their Environment", unpublished, and all documents which that document incorporates by reference, and all applications from which that document claims priority.

BACKGROUND

Field of the Disclosure

This Application generally describes digital eyewear disposed for use with techniques relating to migraines. For example, this Application includes using devices coupled to a patient's senses, and to an ambient environment, to monitor, detect, predict, prevent, and treat migraines, and to train patients to conduct self-care with respect to migraines. This Application also includes other and further techniques.

Related Art

Migraines are a debilitating condition that is remarkably prevalent, affecting an estimated 58 million persons in the United States, and an estimated one billion persons worldwide. Migraines affect about 18% of adult women, 6% of adult men, and 10% of children, and are estimated to affect at least one person in about 25% of households. While most patients' migraine attacks generally occur once or twice per month, some patients suffer from chronic migraines, which can occur 15 or more times per month. About 85% of chronic migraine patients are women.

Public health costs are significant, and can include lost productivity, medical costs, emotional distress, family disturbance, and medication overuse. Annual healthcare and lost productivity costs are estimated at $36 billion, in 2016 US dollars. Migraine patients suffer severely reduced quality of life, substantially higher healthcare costs, limited access to quality healthcare, and are at risk for other physical and psychiatric conditions—such as chronic anxiety, clinical depression, and sleep disorders.

Migraine Symptoms

Migraine symptoms can be severely debilitating, with more than 90% of affected persons unable to work or to function normally during a migraine attack. Migraines can include severe throbbing and reoccurring headache pain (usually on only one side of the head, in contrast with stress headaches). Migraine attacks can last between about 4-72 hours, and typically include pain so severe that the patient is effectively disabled for the duration. In about 15-20% of migraines, patients can notice, for as much as 1-2 days before migraine onset (in a "prodome" portion of a migraine attack), other effects such as constipation, mood changes ranging from depression to euphoria, food cravings, neck stiffness, increased thirst or urination, and frequent yawning.

Migraines can also include incapacitating neurological symptoms, including: visual disturbances, dizziness, nausea, vomiting, extreme sensitivity to senses (including sight, sound, and smell), and tingling or numbness in extremities or the face. About 25% of migraine attacks can include an "aura," a term for a set of nervous system symptoms, such as: visual and tactile hallucinations, loss of sensory acuity, and loss of physical bodily control (including limb weakness). Visual symptoms can include flashes of light, wavy zigzag vision, blind spots, and shimmering spots or "stars". Motor and tactile symptoms can include sensations of pins and needles, asymmetric weakness or numbness, difficulty speaking, tinnitus, and uncontrollable jerking or other movement.

Even after a migraine attack, patients may be affected by unwarranted emotions, such as feeling drained or washed out, or unexpected elation. For about 24 hours thereafter (in a "postdrome" portion of a migraine attack), many patients can experience other effects, including: confusion, moodiness, dizziness, weakness, and sensitivity to light or sound.

Migraines Poorly Understood

Migraines are a poorly understood condition. Some researchers believe that migraines can be caused by neural changes in the brain, by imbalances in brain chemistry: such as an imbalance of serotonin or other neurotransmitters. Some research has shown that women's hormonal changes, such as in a monthly cycle, can trigger a migraine attack, as can certain foods (or lack thereof, e.g., skipping meals or fasting), food additives (e.g., monosodium glutamate), drinks (e.g., wine, other alcohol, caffeine), bright lights, sun glare, loud sounds, strong smells, sleep pattern changes, intense physical exertion, changes in weather (e.g., barometric pressure), certain medications (e.g., oral contraceptives, vasodilators), emotional stress, and other unknown factors. Some research has shown that migraines are a relatively heritable condition, are typically most common from ages 25-55, and affect adult women about three times as frequently as adult men.

Migraines are also associated with relatively rare, but serious conditions. "Retinal migraines" can occur in migraine patients, and can include repeated relatively short bouts of diminished vision or temporary blindness. Retinal migraines affect only one eye, not both; however, loss of vision in a single eye can be caused by other, more serious conditions, and can require medical intervention by a specialist. "Serotonin syndrome" can occur when the brain has much more serotonin than warranted; serotonin syndrome is potentially life-threatening, and can require rapid medical intervention by a specialist. Migraines can also be associated or combined with stroke, internal bleeding in the brain, and other neural infarction.

Known Migraine Treatments

Known treatments include medication for pain relief, and other medication intended to be preventative. Known pain relief medications include: aspirin, ibuprofen, and acetaminophen, which are commonly used for other types of headache. These are sometimes combined with caffeine for mild migraine attacks. Other pain relief medications include: triptans, ergots, anti-nausea medications, opiods, and glucocorticoids. Some of these pain relief medications are also used for their psychoactive effect, and are known to sometimes have significant side effects. Known preventative medications include cardiovascular medication (e.g., beta blockers, also used to treat high blood pressure), antidepressants, anti-seizure medication, and botoxin; certain pain relievers, e.g., naproxen, appear to help prevent migraines and reduce their symptoms.

Nontraditional therapy, such as "alternative medicine," have sometimes been suggested for patients with chronic migraines. Some researchers recommend that patients try one or more of: acupuncture, biofeedback (e.g., relaxation of muscle tension), massage therapy, or cognitive behavioral therapy (e.g., management of how patients perceive pain). There is also some evidence that certain herbs (e.g., feverfew, butterbur) may help prevent migraines or reduce their severity, but study results have been mixed. Similar possibilities have been raised for relatively high dosages of vitamin B2 (riboflavin), for coenzyme Q10 supplements, and for magnesium supplements. However, these alternative treatments do not have any known mechanism reported in the scientific literature.

Some known self-care measures are believed to help alleviate pain due to migraine attacks: muscle relaxation exercises (such as progressive muscle relaxation, meditation, and yoga), consistent and adequate sleep, relaxation (esp. in a quiet unlit room, with application of ice and gentle pressure), and maintaining a "headache diary" to become aware of likely migraine triggers. Similarly, some known self-care measures are believed to help prevent migraine attacks: desensitization to known migraine triggers, a consistent daily schedule, regular exercise, reduced use of estrogen (e.g., as used in birth control pills and hormone replacement therapy). Also, a device ("Cefaly") that performs transcutaneous supraorbital nerve stimulation (t-SNS) has recently been approved by the FDA as a preventative therapy for migraines; research appears to show that this device can help prevent migraine attacks.

When patients are in the midst of a migraine attack, they can be subject to debilitation that disables them from seeking rapid medical treatment. Known medical treatment of migraine attacks as they are in progress typically has only limited effectiveness. The known art with respect to migraines is that they are poorly understood and that medical treatment is often superficial. One consequence is that, in the known art, migraines are a condition that is little understood and not very effectively treated.

Photophobia

One trigger of migraines includes photophobia, such as an abnormal sensitivity to or intolerance of light, especially by the eyes. Photophobia can be triggered by over-stimulation of the retina, such as by excessive luminosity or excessive of luminosity of selected frequencies (such as blue light), excessive stimulus of the optic nerve, and excessive stimulus of brain. Photophobia can even affect the blind. Various causes of photophobia exist throughout the optic system. In addition to possibly triggering (or being triggered by) migraines, photophobia also affects millions of people who otherwise suffer from substantially high sensitivity to light. This can induce symptoms (in addition to migraine symptoms) including severe eye pain, pressure headaches (in addition to and separate from migraine headaches), and degradation of perceptive abilities. Photophobia can itself be debilitating even when it does not also trigger migraines, and is responsible for severe pain, loss of productivity, and reduced quality of life for patients.

One occasional cause of photophobia is failures of photosensitive retinal cells, such as intrinsically photosensitive retinal ganglion cells (ipRGCs). These photoreceptor cells are sensitive to adequate amounts of photopigments, including melanopsin, rhodopsin, and photopsin. Intrinsically photosensitive retinal ganglion cells do not contribute to image formation in the eye, on the retina, or in the brain, but do contribute to the brain's recognition of light levels, such as in the regulation of circadian rhythm. Failure of the eye to contain adequate amounts of melanopsin, rhodopsin, or photopsin, can lead to clinical disorders, including "seasonal affective disorder" (SAD). It can also lead to excessive sensitivity to light, especially blue light and ultraviolet light. It is believed that once intrinsically photosensitive retinal ganglion cells are triggered, they are very slow to return to their un-triggered state, resulting in a sensation of brightness that can cause trouble to those who are sensitive thereto. For example, connections between these sets of light-sensitive cells and the trigeminal system in the brain, particularly in deep brain centers, can cause pain in those who are sensitive thereto. This model of light-sensitivity can explain why the blind can still sense pain from excessive blue light or excessive ultraviolet light.

Neuro-Opthalmic Disorders

Migraines are photophobia are particular instances of a class of neuro-opthalmic disorders, described herein as diseases/syndromes in which patients are excessively sensitive to certain physical stimuli, including audio/visual and other sensory stimuli. For example, unusual sensitivity to excessive luminosity (even if only excessive in a selected range of frequencies, such as blue or ultraviolet light) can trigger symptoms that are temporarily disabling. These symptoms can be as serious as migraines, photophobia, or related disorders. They can include severe eye pain (even for the blind), migraine headaches, pressure headaches, degraded ability to use perceptive senses or motor skills, loss of productivity, and reduced quality of life. When combined with dangerous instrumentalities, such as driving an automobile, or operating heavy machinery or machine tools, negative results can include injury or death.

Each of these issues, as well as other possible considerations, can cause difficulty for patients, particularly during migraine onset or migraine events, symptoms of photophobia, and other neuro-opthalmic disorders. Accordingly, it would be advantageous to provide relief for patients who are subject to migraines, photophobia, neuro-opthalmic disorders, or any combination thereof.

SUMMARY OF THE DISCLOSURE

This summary of the disclosure is provided as a convenience to the reader, and does not limit or restrict the scope of the disclosure or the invention. This summary is intended as an introduction to more detailed description found in this Application, and as an overview of new techniques introduced and explained in this Application. In this Application, the techniques described have applicability in other fields and far beyond the embodiments specifically reviewed in detail.

This Application provides techniques for monitoring, detecting, and predicting migraine onset and migraine events (collectively "migraines" or "migraine activity"), for preventing migraines, for treating migraines (such as in real time), and for training patients to conduct self-care with respect to migraines. This Application provides techniques for monitoring, detecting, predicting, preventing, and treating effects of photophobia, and for training patients to conduct self-care with respect to photophobia (and for combinations of migraines and photophobia). The digital eyewear can maintain information about the progress of migraine onset and migraine events, photophobia effects, and combinations thereof, for each patient individually (and for a set of patients collectively). The digital eyewear can use that information to determine (with or without patient assistance) whether migraine activity or photophobia effects are occurring, or are likely to occur near-term. The digital eyewear can conduct actions that are predicted to ameliorate or treat migraines, photophobia, and combinations thereof. The digital eyewear can train the patient (such as using a reward procedure) to conduct self-care (such as those patient actions beyond the scope of the digital eyewear) that can ameliorate or treat migraines, photophobia, and combinations thereof.

In one embodiment, apparatus including digital eyewear is disposed to receive information from patient sensors and ambient sensors, to maintain a history of patient migraine/photophobia activity and any ameliorative or treatment activity, to determine one or more correlations (such as between those sensors and migraines), to treat migraines/photophobia, and to conduct patient training (such as in response to those sensors and those correlations). For example, the patient sensors can include devices coupled to the patient, and disposed to receive information about the status of the patient. For example, the ambient sensors can include devices coupled to an ambient environment near or coupled to the patient, and disposed to receive information about the status of that ambient environment.

For example, the digital eyewear can receive information from patients with respect to migraine onset and migraine activity, with respect to photophobia effects, and with respect to combinations thereof, can present augmented reality views to ameliorate or treat migraines/photophobia, can present sensory inputs to ameliorate or treat migraines/photophobia, and can reward patients for improvements in self-care with respect to migraines/photophobia. For another example, the digital eyewear can perform these and other procedures for migraines/photophobia in real-time. For another example, the digital eyewear can perform these and other procedures for migraines/photophobia in response to a collective database, such as a collective database that is remotely maintained and is updated with respect to patient information with respect to migraines/photophobia. For another example, the digital eyewear can perform these and other procedures in coordination with other instances of digital eyewear, such as for example coordinating action to ameliorate or treat migraines/photophobia in response to nearby patients and their migraine/photophobia activity (whether self-reported or detected by their own digital eyewear).

In one embodiment, the digital eyewear can determine whether the patient is undergoing migraine onset or migraine events, or photophobia effects, or combinations thereof, such as in response to the patient sensors and the ambient sensors, and such as in response to a record of earlier migraine/photophobia activity (whether migraine onset or migraine events, photophobia effects, or combinations thereof). For example, the digital eyewear can detect migraines/photophobia in response to inputs from the patient with respect to one or more aspects regarded as relevant to migraine onset or migraine events, photophobia, or combinations thereof. For another example, the digital eyewear can detect migraines/photophobia in response to the patient sensors, which can themselves indicate information about the patient that the digital eyewear can process.

In one embodiment, the digital eyewear can predict migraine/photophobia activity, including determining the patient's current likelihood of susceptibility to migraine onset or migraine events, photophobia, or combinations thereof, such as in response to the patient sensors and the ambient sensors, and in response to a record of earlier migraine/photophobia activity (whether specific to migraine onset or migraine events, photophobia, or combinations thereof). For example, the digital eyewear can maintain a set of correlations between patient sensors and ambient sensors, as a first value, and likelihood of migraine/photophobia activity, as a second value. The set of correlations can be responsive to information loaded from medical databases, whether directly coupled or logically remote from the digital eyewear. The set of correlations can also be responsive to information learned from a history of patient activity. For another example, the digital eyewear can conduct a machine learning technique, which can lead to a set of information or procedures that help with predicting migraine/photophobia activity. In such cases, the machine learning can operate either unsupervised, as when the digital eyewear determines when migraine/photophobia activity occurs and learns to predict those occurrences, or supervised, as when the digital eyewear obtains information from the patient re when migraine/photophobia activity occurs and learns to predict those occurrences.

In one embodiment, the digital eyewear can prevent migraine onset or migraine events, photophobia effects, or combinations thereof, (a) such as by altering one or more inputs to the patient's eyes, ears, and other sensory abilities, or (b) such as by altering one or more aspects of the ambient environment. For example, the digital eyewear can be disposed to alter an augmented reality (AR) view presented to the patient, with the effect that the AR view is less likely to trigger migraine onset or migraine events, photophobia effects, or combinations thereof. For example, the digital eyewear can be disposed to reduce light intensity or reduce light intensity in certain frequency ranges, reduce glare, remove undesired visual frequencies, add desired visual frequencies, reduce complexity of the AR view, reduce activity in the AR view, introduce calming elements in the AR view or reduce frequency of transitions or flashing in the AR view, reduce auditory noise, remove undesired auditory frequencies, add desired auditory frequencies, or otherwise modify effects on the patient from sensory inputs, in one or more ways believed to be at least partially effective in ameliorating migraine/photophobia effects. For another example, the digital eyewear can be disposed to alter one or more localized effects, such as temperature, humidity, allergen or pollutant levels, oxygenation for the patient's breathing, or other ambient environmental effects. For another example, the digital eyewear can be disposed to medicate the patient, such as with prescription medication (e.g., sedatives) or non-prescription medication (e.g., antihistamines).

In one embodiment, the digital eyewear can ameliorate or treat migraine onset or migraine events, photophobia effects, or combinations thereof, similar to preventing migraine onset or migraine events, photophobia effects, or combinations thereof. The digital eyewear can be disposed to measure a severity of the migraine/photophobia effects, and possibly to communicate the migraine/photophobia event to medical personnel.

In one embodiment, the digital eyewear can be disposed to train the patient to conduct self-care that can ameliorate or treat migraines/photophobia. For example, the digital eyewear can be disposed to alert the patient when the digital eyewear determines that the likelihood of migraine/photophobia activity is relatively high, or alternatively, substantially higher than normal, and can suggest actions to the patient that can reduce that likelihood. In one such case, when the patient is emotionally upset, and when this is correlated with a higher likelihood of migraine activity, the digital eyewear can alert the patient and suggest that the patient disengage from the emotionally upsetting environment, relax, engage in meditation, take a nap, use a mild sedative, or contact a friend for support. In another such case, when the patient is watching a video image that has excessive flashing or transitions, or is excessively bright, or is excessively bright in certain frequency ranges, the digital eyewear can alert the patient and suggest that the patient disengage from the video image. For another example, the digital eyewear can be disposed to reward the patient for responding to the alert or to the reason for the higher likelihood of migraine activity, with the effect that the patient can learn to respond thereto before the likelihood of migraine activity becomes excessive.

In one embodiment, the digital eyewear can be disposed to monitor, detect, and predict negative visual effects due to changes in lighting conditions, to prevent changes in lighting conditions from causing negative visual effects, and for treating negative visual effects caused by changes in lighting conditions, also in real-time. The digital eyewear can maintain information about changes in lighting conditions, for each patient individually and collectively. The digital eyewear can determine whether changes in lighting conditions, are likely or occurring, and whether consequent negative visual effects are likely or occurring. The digital eyewear can take action to ameliorate any negative visual effects from changes in lighting conditions. As described herein, changes in lighting conditions can include excessive or inadequate light, excessive or inadequate light in a selected frequency range (such as blue light, ultraviolet light, green light, other colors, or improper color balance or mixture), excessive or inadequate light incoming to the patient's eye from a selected direction (such as a peripheral vision direction), or in response to glare or reflection.

This Application also describes use of digital eyewear with other and further techniques with respect to migraines, photophobia, and other neuro-opthalmic disorders.

BRIEF DESCRIPTION OF THE FIGURES

In the figures, like references generally indicate similar elements, although this is not strictly required.

FIG. 3 shows a conceptual drawing of a system including digital eyewear with controllable lenses.

FIG. 4 shows a conceptual drawing of a system including digital eyewear communication.

FIG. 5 shows a conceptual drawing of a method including operation of digital eyewear.

FIG. 6 shows a conceptual drawing of digital eyewear used with augmented and virtual reality.

FIG. 7 shows a conceptual drawing of a method including using digital eyewear with augmented and virtual reality.

Figure 1:
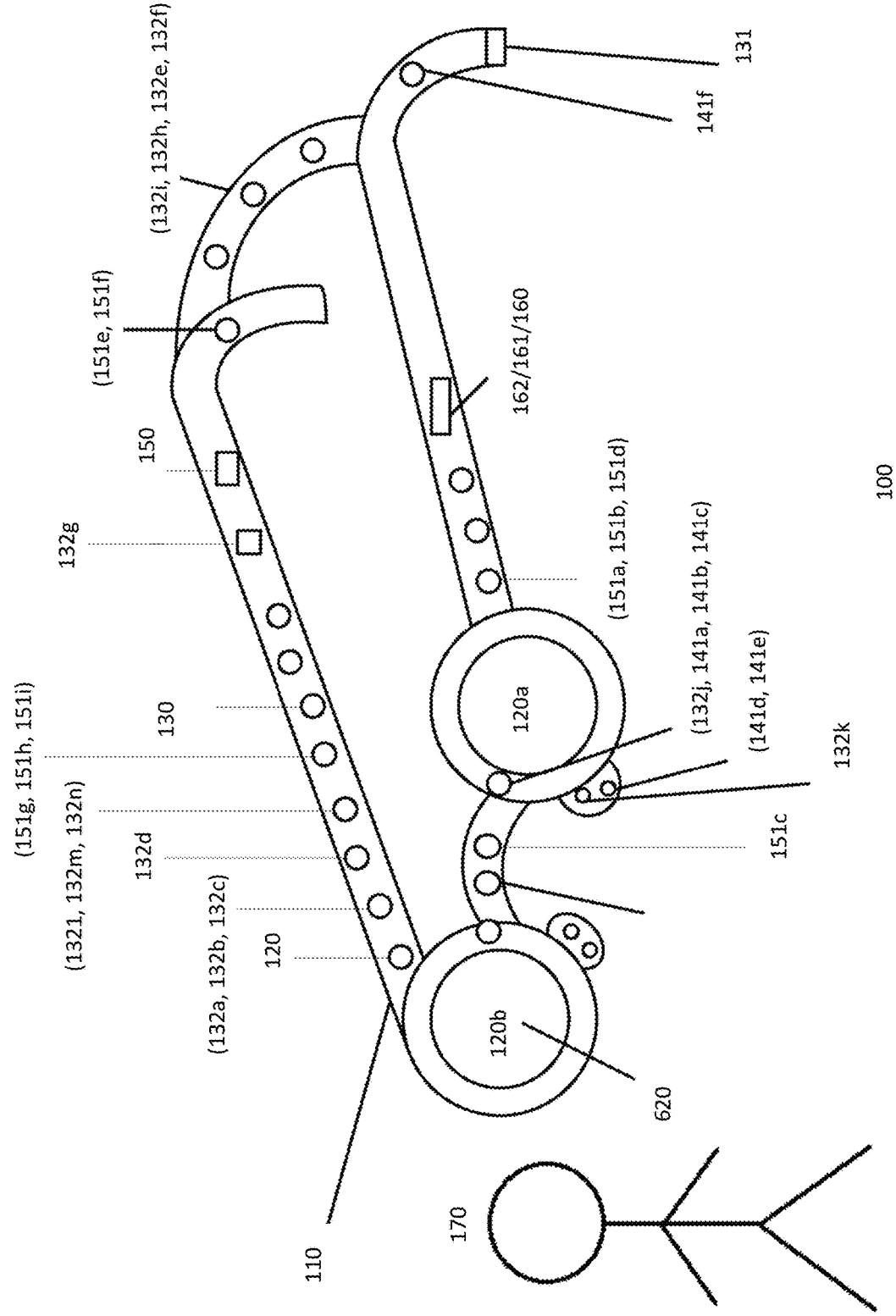
FIG. 1 shows a conceptual drawing of a system including digital eyewear.

After reading this Application, those skilled in the art would recognize that the figures are not necessarily (1) drawn to scale for construction, or (2) specify any particular location or order of construction.

DETAILED DESCRIPTION OF THE DISCLOSURE

Terms and Phrases

The phrase "digital eyewear", and variants thereof, generally refers to any device coupled to a wearer's input senses, including without limitation: glasses (such as those including lens frames and lenses), contact lenses (such as so-called "hard" and "soft" contact lenses applied to the surface of the eye, as well as lenses implanted in the eye), retinal image displays (RID), laser and other external lighting images, "heads-up" displays (HUD), holographic displays, electro-optical stimulation, artificial vision induced using other senses, transfer of brain signals or other neural signals, headphones and other auditory stimulation, bone conductive stimulation, wearable and implantable devices, and other devices disposed to influence (or be influenced by) the wearer.

The terms and phrases "migraine", "migraine activity", and variants thereof, generally refers to any one or more portions of the cluster of symptoms associated with migraines, including the "prodome", "attack", "aura", and "postdrome" portions of migraine events, as well as effects associated with migraines. These terms and phrases also include pain, "retinal migraines", "stars", visual debilitation, inappropriate emotional stimuli, reduced quality of life, and other effects associated with migraines, whether chronic or otherwise.

The phrase "neuro-opthalmic disorder", and variants thereof, generally refers any one or more disorders responsive to audio/visual or other sensory input, and having an effect on perceptive or sensory systems, focus or motor systems, cortical or other thinking systems, or other brain or brain-related systems. For example, as used herein, neuro-opthalmic disorders can include migraines, photophobia, and related syndromes, whether chronic or otherwise.

The term "photophobia", and variants thereof, generally refers to any abnormal or excessive sensitivity to or intolerance of light, especially by the eyes. Photophobia and related effects, as described herein, might be caused by eye inflammation, lack of pigmentation (or loss of pigmentation) in the iris, one or more diseases/syndromes or injuries, or other factors within or without the control of a patient.

The phrase "negative visual effect", and variants thereof, generally refers to any difficulty in sight or vision of a patient, such as those that might occur in response to excessive or inadequate light, excessive or inadequate light in a selected frequency range (such as blue light, ultraviolet light, green light, other colors, or improper color balance or mixture), excessive or inadequate light incoming to the patient's eye from a selected direction (such as a peripheral vision direction), or in response to glare or reflection.

The term "peripheral vision", and variants thereof, generally refers to any portion of sight or vision not directed to a region of the retina in primary focus, or incoming light from a direction not in primary focus. Peripheral vision can include regions to a side of where the patient is directing their focus (sometimes referred to herein as "side to side" peripheral vision), regions higher or lower than where the patient is directing their focus (sometimes referred to herein as "up/down" peripheral vision), or otherwise.

The terms "correlation", "better correlation nature", "better evaluation value", and variants thereof, generally refer to any significant relationship between a first set of values and a second set of values. For example, the term "correlation," when used with respect to conditions that can trigger a patient migraine or photophobia effect, generally refers to any detectable conditions with any substantial relationship to likelihood of triggering a patient migraine or photophobia effect. For another example, "better correlation nature," when used with respect to a method for detecting conditions likely to trigger a patient migraine or photophobia effect, generally refers to any new set of variables or weights, or technique for detection used therewith, having a superior measure of detecting those conditions. Superior measures can include greater accuracy, greater precision of timing, fewer false positives or false negatives, or other statistical measures.

The terms "evaluation", "better evaluation nature", "better evaluation value", and variants thereof, generally refer to any significant relationship between a measurement (or predicted measurement, when the evaluation is a prediction or a predicted evaluation) and an actual degree exhibited by a real-world effect. For example, the term "evaluation," when used with respect to a severity of a patient migraine or photophobia effect, generally refers to any measurement of severity (or optionally, duration) of symptoms affecting the patient. For another example, "better evaluation nature," when used with respect to a method for detecting patient migraines or photophobia effects, generally refers to any new set of variables or weights, or technique for detection used therewith, having a superior measure of evaluating (or predicting) a severity or duration of those conditions.

The terms "predictive", "better predictive nature", "better predictive value", and variants thereof, generally refer to any significant relationship between a measurement to be made in the future, and an actual value of that measurement when it is eventually made. For example, the term "predictive," when used with respect to a severity of a patient migraine or photophobia effect, generally refers to any future measurement of severity (or optionally, duration) of symptoms affecting the patient. For another example, "better predictive value," when used with respect to a method for detecting patient migraines or photophobia effects, generally refers to any new set of variables or weights, or technique for detection used therewith, having a superior measure of predicting a severity or duration of those conditions.

The term "better treatment value", and variants thereof, generally refers to any significant relationship between set of variables or weights, or technique for detection used therewith, and a superior measure of reducing a severity or duration of patient conditions. For example, "better treatment value," when used with respect to a method for detecting patient migraines or photophobia effects, generally refers to any new set of variables or weights, or technique for detection used therewith, having a superior measure of reducing a severity or duration of those conditions.

The term "patient condition", and variants thereof, generally refers to any condition, or measure thereof, detectable by patient sensors, patient self-reports, or observation of the patient. For example, patient conditions can include patient eye activity, patient head or body movement, patient speech/vocalization, patient migraine/photophobia diary entries, observations of patients by medical personnel or emergency responders, and otherwise.

The terms "augmented reality", "augmented reality view", "AR", "AR view", and variants thereof, generally refer to any alteration of patient sensory inputs. For example, an "augmented reality view" can refer to an external reality view that has been adjusted by shading/inverse-shading with respect to light intensity or audio intensity (whether for a broad spectrum or limited to selected frequencies), such as by removing excessive glare or other impairments to visual acuity. For another example, an "augmented reality view" can refer to an external reality view that has been adjusted by inserting/removing selected images not located (or not located in the same place or time) in the external reality view, such as by inserting text, icons, or chyrons having information for the patient, or such as by moving elements of the external reality view within the patient's point of view, to improve visual acuity. For another example, an "augmented reality view" can refer to a view presented to the patient that has little or nothing to do with an external reality view, and is generated for use by the patient without necessarily referencing external reality, such as a meditative environment or other set of perceptual inputs deemed good for the patient at that moment, or such as a set of perceptual inputs deemed useful for determining the patient's relative susceptibility to migraine/photophobia from a selected perceptual effect.

The term "external reality view", and variants thereof, generally refers to any collection of patient sensory inputs substantially dictated by forces external to the digital eyewear. For example, an "external reality view" can refer to an audio/visual image that would be otherwise received by the patient, such as a natural scenic view, a view of a sports or other event, a view of a person with whom the patient is conversing, a movie or other external audio/visual presentation, a remote view (such as via telescope or CCTV, or presented from a camera attached to an unmanned vehicle) of an astronomical or other natural event, or an audio/visual feed otherwise not specifically generated by the digital eyewear.

The term "real time", and variants thereof, generally refers to any function or operation performed without substantial delay, such as without a significant processing delay. For example, determining an augmented reality view in real time can include making the determination within a time period not recognizable as delay by a human patient. For another example, determining a likelihood of an upcoming event (such as a patient migraine or patient photophobia effect) in real time can include making the determination within a time period substantially before the actual upcoming event. For another example, determining an augmented reality view in real time can include making the determination with a delay, while buffering the augmented reality view for presentation to the patient, with the effect that the patient feels the presentation is made without substantial delay, or without video jitter, pauses, or skips.

FIGURES AND TEXT

FIG. 1

FIG. 1 shows a conceptual drawing of a system including digital eyewear.

The system can be described herein with respect to elements shown in the figures, such as:
 digital eyewear 100;
 an eyewear frame 110;
 one or more eyewear lenses 120;
 a set of patient sensors 130, including at least one or more input/output elements 131 coupled to the patient, and other example patient sensors as described herein;
 a set of ambient sensors 140, including example ambient sensors as described herein;
 a set of treatment devices 150, including example treatment devices as described herein;
 a control element 160, including at least a computing device 161 having a processor, program and data memory, and input/output elements coupled to the patient sensors, the ambient sensors, and the treatment devices; and a communicator 162 having a sending/receiving element.
 a patient 170 or other wearer, who is of course not part of the digital eyewear.

The digital eyewear 100 can be disposed for coupling to the patient 170. For example, the patient 170 can wear the eyewear frame 110. For another example, the digital eyewear 100 can be coupled, such as by a Bluetooth™ or other wireless connection to another wearable device, which can be worn by the patient 170 or other wearer. Other wearable devices can include a wristband, such as a FitBit™, a glove, a headband, a necklace, one or more earrings, or other accessories, any of which can be worn by the patient 170 or other wearer. For another example, the digital eyewear 100 can be coupled to a mobile device, such as a cell phone, music player, or similar device, which can be carried or operated by the patient 170 or other user. For another example, the digital eyewear 100 can include or be coupled to one or more contact lenses, which can be worn by the patient 170 or other wearer. For another example, the digital eyewear 100 can include or be coupled to one or more implantable devices, such as an implantable lens (or replacement lens in the eye), a subcutaneous device, or one or more nanodevices or other devices suitable for operating inside the body, which can be coupled to the patient 170 or other user.

Eyewear Frame

Figure 2:
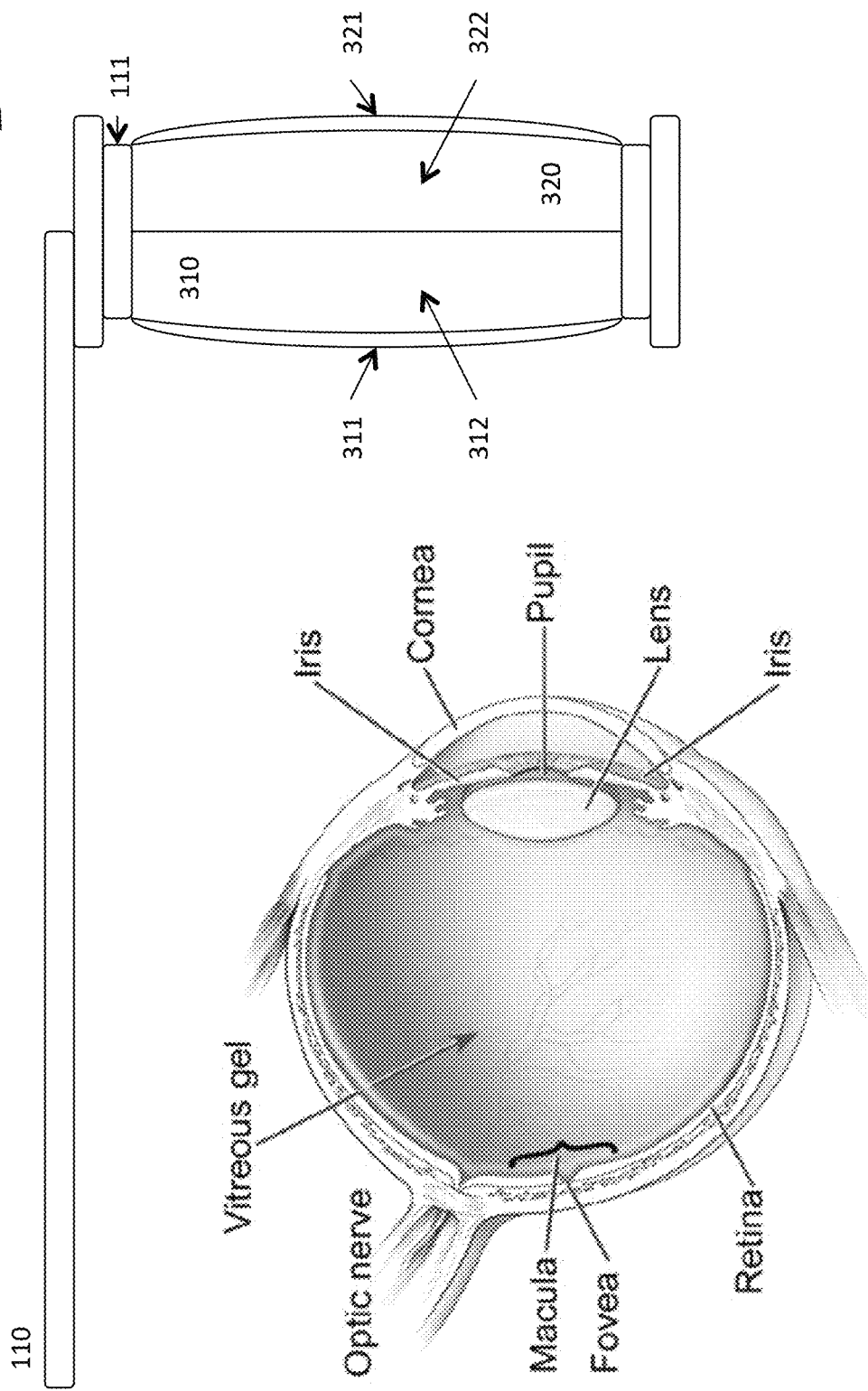
FIG. 2 (collectively including panels A, B, C, D, and E) shows a conceptual drawing of some alternative embodiments of the digital eyewear.

In one embodiment, the eyewear frame 110 is disposed to support the eyewear lenses 120, the patient sensors 130, the ambient sensors 140, the treatment devices 150, and the control element 160. Alternatively, one or more devices otherwise supported by the eyewear frame 110 can be disposed in, on, or near the patient 170, with the effect that the digital eyewear 100 can include devices that intercommunicate to exchange information. As described herein, FIG. 2 shows some alternative embodiments of the digital eyewear. In such alternative embodiments, it may occur that one or more such devices can be dynamically swapped out in exchange for new devices, from time to time, or that one or more such devices can cooperate with devices supporting another digital eyewear 100.

When devices supporting multiple digital eyewear 100 systems communicate, they can gather information about a greater area near the patient 170 (or a greater area near multiple such patients 170 or other users), can determine if the patient sensors 130 are detecting information unique to the patient 170 or shared by more than one patient 170, and can determine whether the ambient environment is affecting one patient 170 substantially more than others. As described herein, FIG. 4 shows a system including digital eyewear communication.

Lenses

In one embodiment, the eyewear frame 110 can support the eyewear lenses 120. For example, the eyewear lenses 120 can include a left-eye lens 120*a* disposed to present information to the patient's left eye, and a right-eye lens 120*b* disposed to present information to the patient's right eye. The lenses 120 can be disposed to present information in one or more ways:

For a first example, the lenses 120 can include a substantially transparent element disposed to allow through passage of light from external sources, wherein the transparent element can be controlled to block passage of some or all of the light into the eye from specified locations (e.g., pixels) or control some or all of the light passing through the entire lens, and at specified frequencies (e.g., 450-490 nm blue), and wherein the transparent element can be controlled to allow or emit light into the eye from specified locations (e.g., pixels) and at specified frequencies (e.g., 520-560 nm green). This can have the effect that the lenses 120 show the patient 170 an external image, modified as desired by the control element 160. This can have the effect that the control element 160 can reduce or increase the intensity of an incoming image, reduce or increase the intensity of selected frequencies in an incoming image, replace selected frequencies in an incoming image with distinct other frequencies, and replace the incoming image with another image. When the control element 160 alters the incoming image, it can alter all of it, or only a selected portion thereof.

For a second example, the lenses 120 can include a substantially opaque element disposed to block and measure incoming light from external sources, wherein the control element 160 can determine an incoming image, without necessarily allowing that incoming image to reach the eye. The substantially opaque element can include, or alternatively be paired with, a mirror or screen at which the control element 160 can direct light so as to be reflected into the patient's left eye, patient's right eye, or both. This can similarly have the effect that the lenses 120 show the patient 170 an external image, modified as desired by the control element 160. In such second examples, this can have the effect that the control element 160 can alter the incoming image, or only a selected portion thereof, as described above with respect to the first example. In such second examples, the mirror or screen does not need to be collocated with the lenses 120. They can instead be disposed as in a retinal image display, with the effect that the control element 160 can emit light directly into the eye, such as from a laser or a filtered white light source.

For a third example, the control element 160 can determine a gaze direction and focal length for each eye (wherein the gaze direction and focal length of the left eye and right eye should match), and can direct the lenses 120 to show only the portion of the external image selected by the eyes, as modified as desired by the control element 160. In such third examples, the lenses 120 can be disposed to render only those portions (e.g., pixels) of the external image within the focused-upon area selected by the eyes, or to render those portions at a lower resolution or intensity, even if other portions of the external image are of interest. In such third examples, similar to the first and second examples, the lenses 120 can be either substantially transparent by default or substantially opaque by default, with the control element 160 deciding what image to present to the patient 170. Also in such third examples, similar to the second examples, the lenses 120 can use a retinal image display, with the effect that the control element 160 can emit light directly into the eye.

In one embodiment, the lenses 120 can include multiple digital lenses, multi-layered lenses or multi-coated lenses, such as the following (shown in FIG. 3):

a first layer 310, including one or more of: a lens, a lens layer, or a lens coating;

a second layer 320, including one or more of: a lens, a lens layer, or a lens coating;

In one embodiment, each of the first layer 310 and the second layer 320 can be static (that is, having a substantially constant effect) or electrodynamic (that is, responsive to an electromagnetic or other control signal).

In one embodiment, the first layer 310 can include an anti-reflective effect responsive to selected frequencies of electromagnetic radiation, with the effect of reducing a selected electromagnetic frequency (such as blue light, ultraviolet A or B radiation, or otherwise).

In one embodiment, the second layer 320 can include a shading effect, possibly responsive only to an intensity of electromagnetic radiation (that is, monochrome), or alternatively responsive to selected frequencies of electromagnetic radiation, with the effect of shading/inverse-shading. For example, the second layer 320 can include a fast-acting adaptive shading element (such as using LCD or other techniques) and can be disposed for relatively rapid control of light intensity. For another example, the second layer 320 can include an adaptive electrochromatic effect, with the effect that it can be disposed either (a) in a clear state, or (b) in a filtering state in which is allows selected frequencies (such as a specific color of light, such as green light) to pass through to the patient's eye.

In one embodiment, the combination of the first layer 310 and the second layer 320 can be disposed both (a) to remove rapid bursts of light, and (b) remove dangerous frequencies of light, while still allowing passage of valuable frequencies of light.

In one embodiment, the lenses 120 can include eyeglass lenses (such as those disposed in an eyeglass frame, and generally disposed between the eye and external images), contact lenses (such as those disposed on the surface of the eye, and generally disposed to cover the pupil with respect to external images), implantable lenses (such as those disposed below the surface of the eye, or to replace the natural lens of the eye, and generally disposed to interpose between the retina and external images), or otherwise.

In one embodiment, the lenses 120 can be disposed between the patient's vision and external images in front of the patient 170, in the peripheral vision (side to side) of the patient 170, and between the patient's vision and other directions (such as from above, from below, and from behind such as reflecting off the eyeware frame 110 or the lenses 120 themselves).

Patient Sensors

In one embodiment, the eyewear frame 110 can support one or more of the patient sensors 130. Patient sensors can include (a) input from the patient 170, such as motion of the hands, fingers, arms, head, neck, or other body parts; (b) sensors coupled to the patient's eyes, ears, nose, skin, or other bodily senses; (c) sensors coupled to the patient's brain activity, motor and related nerve activity, surface fluids or moisture, internal/surface temperature, or other bodily responses; (d) sensors coupled to the patient's cardiovascular activity, such as heart rate, oxygenation activity, breathing rate/moisture/oxygenation, blood oxygenation, or other bodily system activity; (e) sensors coupled to the patient's menstrual cycle, fluid intake, perspiration, alcohol/drug products, urine/fecal matter, or other bodily statuses; or other devices disposed to receive information with respect to the patient 170.

For example, the patient sensors 130 can include one or more of the following:

A pupillometry sensor 132a disposed to conduct real-time measurement of pupil width, as well as at least a first and second time-derivative thereof, and at least a first and second statistical moment thereof. The pupillometry sensor 132a can include a camera or other light-sensitive (or sensitive to other frequencies, such as infrared or ultraviolet) element, disposed to measure pupil width, and sending its measurements to the computing device 161. The computing device 161 can be disposed, such as by its processor executing instructions in memory, to determine the first and second time-derivative; if the derivatives (or the size of the derivatives) are too large, the control system 160 can determine that the patient 170 is subject to a migraine (or at least subject to substantial emotional stress, which can be correlated with migraines, photophobia, and other deleterious effects). The pupillometry sensor 132a can also include a sonar sensor, such as one using ultrasound to determine locations of edges of the pupil, operating either in concert with or lieu of an electromagnetic sensor.

In one embodiment, the control system 160 can determine (such as when the pupillometry sensor 132a indicates a sudden widening of the pupils) that the patient 170 is under substantial emotional stress. Substantial emotional stress can be correlated with migraine onset.

Substantial emotional stress can also be correlated with severe pain, such as can occur in response to (1) photophobia, or (2) excess light input to the eye, such as can occur when the patient 170 is performing in an overly-bright environment. For example, if the patient 170 is in severe pain, this can be due to photophobia, due to direct viewing of sunlight, or due to sudden glare. For another example, if the patient 170 is participating in a sport, excess light input to the eye can result from having the sun in view, from having the eyes adjusted to a cloudy day and having the clouds move away, or from reflective glare (such as from bodies of water, metallic surfaces, and reflections from windows or other glass objects). Glare is not necessarily limited to outdoor events, as it can result from reflection from artificial lighting. In any of these possible events, it can be desirable to adjust a degree of shading/inverse-shading to decrease an amount of light allowed into the eye, with the effect of reducing pain due to excess light.

As described herein in other and further detail, excess light input to the eye might be particularized to specific frequencies, such as blue light or ultraviolet light. It is believed that both blue light and ultraviolet light can stimulate particular cones (color-detecting cells in the retina). This can send a strong light intensity signal to the brain, and can inform the brain that the eye is in pain. Alternatively, even patients 170 who are blind can suffer the effects of nerve signals directed to the brain from cone cells. Thus, even if total luminance is within an acceptable range, blue-light or ultraviolet-light luminance can exceed reasonable and produce eye pain. Patients 170 with photophobia, who are sensitive to bright light, can be particularly sensitive to blue light and ultraviolet light. In any of these possible events, it can be desirable to adjust a degree of shading/inverse-shading to decrease an amount of into light for these particular frequencies.

As also described herein in other and further detail, excess light can also be input to the eye from particular directions, such as from the eye's peripheral vision. Although the light sensing cells used for peripheral vision are believed to be less sharp than near the focus of vision, those light sensing cells can still be overly stimulated by excess light, even when that light arrives from a peripheral direction. In such cases, excess light from a peripheral direction can cause severe pain, particularly for those patients 170 who have photophobia. Excess light from a peripheral direction can even cause severe pain for patients 170 who do not have photophobia, but who are not prepared. For example, such patients can be involved in a sporting activity where light conditions change quickly. Excess light from a peripheral direction can also trigger migraine onset. In any of these possible events, it can be desirable to adjust a degree of shading/inverse-shading to decrease an amount of into light from a peripheral direction.

As also described herein in other and further detail, the presence of excess light can be, at least in part, predicted by the digital eyewear 100, such as by its control element 160. The effect of excess light can be alleviated by the digital eyewear 100, such as by shading/inverse-shading of the lenses 120. In such cases, when the digital eyewear 100 is able to predict with reasonable certainty that excess light is about to be received by the eye, the control element 160 can control the lenses 120 to invoke shading/inverse-shading. This can have the effect of reducing or eliminating a possible source of pain, thus reducing the possible effects of migraines or photophobia.

As also described herein in other and further detail, the presence (or predicted presence) of excess light can be identified by the digital eyewear 100, such as when the patient 170 is engaged in a sport activity, other outdoor activity, or an indoor activity in which light conditions are variable. For example, activities can include participation in a sport activity or watching a sport activity, such as (in the case of recreation) exercise, hiking, camping, and similar activities, or such as (in the case of professional activities) search and rescue operations, firefighting, or police or military activity. Activities can include driving. In such cases, the digital eyewear 100 can detect or predict, at least in part, excess light that might have the effect of distracting the patient 170, or otherwise reducing visibility. For example, sudden changes in amount of light, due to weather or other changes, or sudden changes in visibility, due to glare or other effects, can be ameliorated by the digital eyewear 100 upon prediction or detection, using shading/inverse-shading. The shading/inverse-shading can be particularized to specific frequency ranges (such as blue light or ultraviolet light) or to specific directions (such as peripheral vision).

As described herein, the pupillometry sensor 132a can be coupled to a shading/inverse-shading device, to provide shading/inverse-shading in response to the patient's eye. In addition, as described herein, the shading/inverse-shading device can be coupled to and responsive to one or more of: optical/perceptual parameters, parameters personalized to the patient 170, or the patient's mental state. As described herein, the optical/perceptual parameters, parameters personalized to the patient 170, or the patient's mental state, can be derived from one or more of the patient sensors 130, the ambient sensors 140, or feedback from the treatment devices 150.

A gaze direction and focal length sensor 132b disposed to conduct real-time measurement of gaze direction and focal length for each eye, as well as at least a first and second time-derivative thereof, and at least a first and second statistical moment thereof (similar to the pupillometry sensor 132a). The gaze direction and focal length of the left eye and right eye should match; if not, the control element 160 can determine that the patient 170 either (a) is sleep deprived or otherwise at least partly unable to focus properly, or (b) is subject to a migraine and has lost at least some control of their ability to focus properly. Similar to the pupillometry sensor 132a, if the derivatives of gaze direction or focal length are too large, the control system 160 can determine that the patient is subject to a migraine.

A blink rate sensor 132c disposed to measure real-time blink rate of the patient's eyes. The control system 160 can determine at least first and second time-derivatives of, and at least first and second statistical moments of, the blink rate (similar to the pupillometry sensor 132a). The control system 160 can use the blink rate to determine a measure of dryness of the eye, irritation of the eye, and possibly other features with respect to the patient 170. Excessive dryness of the eye can be correlated with migraine/photophobia.

In one embodiment, the blink rate sensor 132c can include a camera disposed to view the eyelid, or a portion thereof, and instructions at the computing device 161 to determine how frequently the eyelid moves from open to closed or from closed to open. For example, the blink rate sensor 132c can include a camera disposed to view the iris or pupil, or a portion thereof, and instructions at the computing device 161 to determine how frequently the eyelid obscures the iris or pupil. For another example, the blink rate sensor 132c can include a camera disposed to view, or another sensor disposed to measure, a reflectivity of the sclera (such as an infrared reflectivity), or another portion of the eye or a portion thereof, and instructions at the computing device 161 to determine a measure of dryness of the sclera or other portions of the eye.

In one embodiment, the blink rate sensor 132c can include a capacitive measure of the eye, such as an electrooculgraphy (EOG) sensor, which can determine how frequently the capacitive measure of the eye changes in response to an eyeblink. The EOG sensor can also measure a differential retinal response between a lighter image and a darker image, such as by measurement of the Arden ratio, with the effect that the EOG sensor can also be used to determine a relative light sensitivity of the eye. The EOG sensor can also be used to determine frequency, rapidity, and direction of eye movement, in response to capacitive changes from changes in gaze direction. The control system 160 can determine at least first and second time-derivatives of, and at least first and second statistical moments of, the EOG sensor (similar to the pupillometry sensor 132a).

An electroencephalography (EEG) sensor 132d disposed to measure real-time brain activity of the patient 170. The control system 160 can, in response to a total electroencephalography signal, and first and second time-derivatives thereof (similar to the pupillometry sensor 132a), can determine a total excitivity of the brain. Similar to the pupillometry sensor 132a, if the derivatives (or the size of the derivatives) are too large, the control system 160 can determine that the patient 170 is subject to a migraine.

An electromyography (EMG) sensor 132e disposed to conduct real-time measurement of muscle tone of the patient's head and neck, as well as at least a first and second time-derivative thereof, and at least a first and second statistical moment thereof (similar to the pupillometry sensor 132a). Muscle tone or skin elasticity can also be measured using stress sensors, such as electrical circuits, electromotor sensors, skin elasticity sensors, strain gauges (metallic or otherwise), and other sensors disposed to determine effects of migraines on musculature.

In one embodiment, the digital eyewear 100 can also use the EMG sensor 132e to determine if the patient 170 has eyestrain or a tension headache, if they do not also have a migraine/photophobia. It might occur that severe eyestrain or a severe tension headache can be correlated with migraine onset, or with onset or continuation of one or more photophobia effects.

An electrocardiography (ECG) sensor 132f disposed to conduct real-time measurement of cardiac signals, from which the computing device 161 can determine the patient's heart rate, as well as at least a first and second time-derivative thereof, and at least a first and second statistical moment thereof (similar to the pupillometry sensor 132a). The control element 160 can use heart rate to assist in determining whether the patient 170 is having an unusual emotional response, such as undue stress.

One or more accelerometers 132g disposed to determine measure physical exertion, such as running or other physical exercise. For example, accelerometers 132g can help determine whether the patient 170 is running or jogging when their heart rate is elevated, which can help the control system 160 determine whether the ECG sensor 132f measurements indicate exercise (e.g., running or jogging) or pain or another emotional response (e.g., due to migraine/photophobia). For another example, the accelerometers 132g can help the control system 160 determine whether the patient 170 is subject to unusual acceleration (such as in a roller coaster or a careening motor vehicle), which can help the control system 160 determine whether the ECG sensor 132d measurements distinguish between different emotional responses (e.g., excitement or fear, pain or anxiety, or otherwise).

A skin galvanometer 132h disposed to measure real-time conductivity of the patient's skin and capacitance of the patient's outer skin layers, such as at areas of the head and neck. The skin galvanometer 132h can include, or be combined with, a specific perspiration detector disposed to measure real-time concentrations of moisture and electrolytes on the patient's skin, such as at similar or symmetrically identical areas. The computing device 161 can be disposed to determine at least a first and second time-derivative thereof, and at least a first and second statistical moment thereof (similar to the pupillometry sensor 132a). For example, skin conductivity and capacitance can help the control system 160 determine whether the patient 170 is dehydrated, as dehydration can be correlated with migraines/photophobia.

A blood oxymeter 132i disposed to measure oxygenation of the patient's blood, or another measure of adequate supply of oxygen to the patient's brain and nervous system. The computing device 161 can be disposed to determine at least a first and second time-derivative thereof, and at least a first and second statistical moment thereof (similar to the pupillometry sensor 132a). Lack of blood oxygenation, or rapid changes thereof, can be correlated with migraines/photophobia. For a first example, the blood oxymeter 132i can be coupled to a relatively transparent portion of the patient's external body, such as a finger or earlobe (or in the case of a neonate or a small child, a toe, foot, or palm). The computing device 161 can be disposed to determine blood oxygenation in response to a ratio of blood reflection or transmission of red and infrared light. For a second example, blood oxygenation can be determined in response to coloration of the retina, such as measured by (visual and IR) cameras directed at portions of the retina. Frequency analysis of blood oxymetry can also help the control system to determine a heart rate, e.g., by measurement of a primary frequency of change in blood oxymetry.

A microphone 132j or other vibration sensor, disposed to measure real-time breathing rate, such as at areas of the head and neck. The computing device 161 can be disposed to determine at least a first and second time-derivative thereof, and at least a first and second statistical moment thereof (similar to the pupillometry sensor 132a). For example, microphones 132j can measure both breathing rate and whether the patient's breathing is relatively shallow or deep. Microphones 132j can be combined with one or more $CO_2$ sensors, or other sensors of breathing products, disposed (such as on the digital eyewear near a nosepiece, or near the patient's mouth or nose). For example, $CO_2$ sensors can help the control system 160 determine whether the patient 170 is receiving adequate oxygenation.

A camera 132k or other motion sensor (such as an infrared motion sensor, sonar or ultrasonic sensor, or vibration sensor), directed at the eyelid and disposed to measure realtime blink rate. The computing device 161 can be disposed to determine at least a first and second time-derivative thereof, and at least a first and second statistical moment thereof (similar to the pupillometry sensor 132a).

One or more intake/outgo sensors 132l disposed to measure the patient's fluid intake, exhalation, perspiration, and dry substance intake (e.g. grains). For example, substance intake can be measured in response to self-reporting by the patient 170, while exhalation and perspiration can be measured in response to a moisture gradient emanating from the patient 170 (or from specific patient 170 orifices, such as the mouth or nose). The computing device 161 can be disposed to determine at least a first and second time-derivative thereof, and at least a first and second statistical moment thereof (similar to the pupillometry sensor 132a).

One or more sleep sensors 132m disposed to measure sleep deprivation, such as the patient's past night's sleep, a patient's recent nap, the patient's eye focus, and the patient's reaction time. For example, past night's sleep and recent nap can be measured in response to self-reporting by the patient 170, or in response to a bodily movement sensor and temperature sensor. For another example, the patient's eye focus and reaction time can be measured by a camera directed at the iris and pupil of the patient's eyes, such as determining a clarity and regularity of focus and a speed of eye reaction to new stimuli. The computing device 161 can be disposed to determine at least first and second time-derivatives thereof, and at least first and second statistical moments thereof (similar to the pupillometry sensor 132a), as eye focus and reaction time might be correlated with whether the patient 170 is preoccupied with other matters.

One or more menstrual sensors 132n disposed to measure the patient's menstrual cycle (for patients 170 who actually have menstrual cycles). For example, the patient's menstrual cycle can be measured in response to bodily temperature, or as otherwise in known use for measuring menstrual cycle, or in response to requesting the information from the patient 170. Adult women are much more likely to have migraine attacks than adult men; researchers believe this is correlated with the menstrual cycle.

In one embodiment, the patient sensors 130 can be responsive to one or more medical records associated with the patient 170. The medical records can be retrieved ahead of time, before incoming audio/video signals to be presented to the patient 170, and processed by the control element 160 to assess possible patient 170 sensitivity to incoming audio/video signals. The medical records can be retrieved dynamically in response to ability to retrieve those records, such as when those records can be retrieved in response to presence in a medical office.

Ambient Sensors

In one embodiment, the eyewear frame 110 can support one or more of the ambient sensors 140. Ambient sensors can include sensors (a) coupled to ambient light: such as brightness, frequency, and variance; or sound: such as loudness, frequency, variance, and noise; (b) coupled to ambient weather conditions: such as temperature, humidity, air pressure, pollen counts, electromagnetic flux and UV index, ionization or other measures of pollutants; (c) coupled to physical location: such as GPS coordinates, elevation, or other indicators of possible migraine-coupled activity; (d) coupled to other patients 170: such as by communication with other digital eyewear and deduction/induction from other patients' migraine onset or activity; or other sensors that could bear on or be correlated with migraine onset or activity.

For example, the ambient sensors 140 can include one or more of the following:

A light spectrum sensor 141a disposed to conduct real-time measurement of a frequency distribution in ambient light, such as incoming light in an image at which the eyes are directed. The light spectrum sensor 141a can determine a relative fraction of incoming light at each known frequency or frequency band, such as frequency bands designated for infrared (approximately >1000 nm), red (approximately 635-700 nm), green (approximately 520-560 nm), blue (approximately 450-490 nm), and ultraviolet (approximately <500 nm). Blue light and ultraviolet light can be correlated with migraines, while green light can be correlated with preventing or ameliorating migraines. In one embodiment, the light spectrum sensor 141a can be combined with measurements of the patient's iris and lens, and any corrective lenses or shading/inverse-shading lenses used by the patient 170, as those eye components and external lenses can have filtering effects on incoming light. The computing device 161 can be disposed to determine at least a first and second time-derivative thereof, and at least a first and second statistical moment thereof (similar to the pupillometry sensor 132a), as rapid variation in light spectrum can be correlated with migraines.

A light intensity sensor 141b disposed to conduct real-time measurement of incoming light to the patient's eye (such as total candelas/square-meters received by each eye). The light intensity sensor 141b can be disposed to measure light intensity at known frequencies of light; while relatively lower light intensity can be correlated with ameliorating migraines, it can be desirable to maintain relatively higher light intensity in the green (520-560 nm) color range anyway. The computing device 161 can be disposed to determine at least a first and second time-derivative thereof, and at least a first and second statistical moment thereof (similar to the pupillometry sensor 132a), as rapid variation in light intensity can be correlated with migraines.

As described herein, the light intensity sensor 141b can be coupled to the control element 160, with the effect that the control element 160 can determine when an amount of light intensity exceeds a first selected threshold beyond which pain occurs, or a second selected threshold beyond which there is a significant threat of migraine onset. The first selected threshold and the second selected threshold can be determined in response to medical guidelines and in response to input from the patient 170. Medical guidelines can be received from data repositories 420 or treatment servers 430. Input from the patient 170 can be received from patient sensors 130 or input/output devices coupled to the control element 160. As described herein, when excess light is detected or predicted (or when excess light in selected frequency ranges, such as blue light or ultraviolet light, is detected or predicted) the control element 160 can direct the lenses 120 to shade/inverse-shade. This can have the effect that excess light on the patient 170 is reduced in effect. This can have one or more of the following effects: (1) reducing the chance of migraine onset, (2) reducing the severity or duration of a current migraine, (3) reducing the chance of a photophobia effect, (4) reducing the severity or duration of a photophobia effect, or a combination thereof.

As also described herein, when the patient 170 is engaged in a sport activity, other outdoor activity, or an indoor activity in which light conditions are variable, the light intensity sensor 141*b* can be coupled to the control element 160 to reduce any negative effects of changes in light conditions. Negative effects can include reduced visibility (such as due to a time needed for the patient's pupil to react to changes in light conditions, or such as due to excess light flooding images needing relatively fine distinctions in light intensity), distraction (such as due to the patient's attention being drawn to changes in light conditions, or such as due to glare affecting the patient's vision), or otherwise. For example, the patient's ability to distinguish small objects, such as a ball in a sporting event, or such as a distant target in a search/rescue activity or police/military activity, can be affected by changes in lighting conditions, and particularly by sudden brightness/darkness or by glare. In such cases, the control element 160 can direct the lenses 120 to shade/inverse-shade to reduce the amount by which the change in lighting condition affects the patient's vision.

A light polarization sensor 141*c* disposed to conduct real-time measurement of what fraction of incoming light to the patient's eye is polarized. For example, reflected light (such as glare, light reflected from a seascape, or otherwise) is primarily polarized. The computing device 161 can be disposed to determine at least a first and second time-derivative thereof, and at least a first and second statistical moment thereof (similar to the pupillometry sensor 132*a*), as rapid variation in polarization can be correlated with sudden glare, which can be correlated with migraines.

As described herein, the light polarization sensor 141*c* can also at least in part, detect glare.

One or more weather measurement sensors 141*d*, including sensors for barometric pressure, humidity, and temperature. For example, cold and dry weather can be correlated with migraines. The computing device 161 can be disposed to determine at least a first and second time-derivative thereof, and at least a first and second statistical moment thereof (similar to the pupillometry sensor 132*a*), as rapid variation in weather can be correlated with migraines.

One or more ambient irritant measurement sensors 141*e*, including sensors for pollutants (such as chemical, ionizing, or particulate pollutants), pollen count, and other triggers for eye/sinus irritation, irritation of other membranes or portions of the patient's body, or triggers for other allergies or headache-inducing factors. Known pollutants can include NOx, ozone, particulates (such as dust or soot), sulfur compounds, unburned hydrocarbons, vehicle exhaust, and other chemical or physical detritus. Pollen count, for one or more of at least 12 or more known different types of pollen, can be measured either directly, or by reference to a GPS sensor coupled to a database or weather report of pollen counts. The computing device 161 can be disposed to determine at least a first and second time-derivative thereof, and at least a first and second statistical moment thereof (similar to the pupillometry sensor 132*a*). For example, the ambient irritant measurement sensors 141*e* can be disposed on or near the digital eyewear (or a related device), on or near the patient 170, or collected from external databases in response to a location, time/date, or elevation of the patient 170. In such cases, the ambient irritant measurement sensors 141*e* can obtain information from the location/movement sensors 141*f* (possibly including GPS sensors, as described herein), and obtain information from one or more remote data repositories 420 or treatment servers 430 in response thereto (as described herein).

One or more location/movement sensors 141*f*, possibly including GPS sensors, wireless network triangulation sensors, accelerometers, altimeters, magnetic compasses, gyroscopes (mechanical, optical, or otherwise), or other devices suitable for determining absolute location, orientation, velocity, acceleration, or angular momentum. The computing device 161 can be disposed to determine at least a first and second time-derivative thereof, and at least a first and second statistical moment thereof (similar to the pupillometry sensor 132*a*), as rapid changes in location or momentum can be of use in determining factors correlated with migraines.

In one embodiment, the control element 160 can be disposed to use the communicators 162 to access data repositories 420 (shown in FIG. 4) or treatment servers 430 with respect to information from the location/movement sensors. For example, the data repositories 420 can report information for light intensity, UV flux, weather measurement, ambient irritants, and other real-time data associated with the patient's location. For example, requests for treatment assistance can be routed to treatment servers 430 identified with the patient's location; when needed, medical personnel and emergency responders can be contacted in response to the patient's location.

Treatment Devices

In one embodiment, the eyewear frame 110 can support one or more of the treatment devices 150.

Treatment devices can include elements (a) disposed to filter light incoming or otherwise input to the patient's eyes, such as light that is overly intense, overly rapidly changing, overly complex, or includes frequencies unduly likely to trigger a migraine; (b) disposed to filter sound or smells incoming or otherwise input to the patient's senses, such as sound that is overly loud, overly rapidly changing, overly complex, or includes frequencies unduly likely to trigger a migraine, or such as smells that are overly intense or, by the patient 170, associated with substances or events with strong emotional context; (c) disposed to inject light or other inputs to the patient's senses intended to reduce the likelihood of a migraine, or to reduce the effect of a migraine that is occurring; or (d) disposed to assist the patient 170 in self-care to reduce the likelihood of a migraine, or to reduce the effect of a migraine that is occurring. For example, one or more treatment devices can incorporate pharmaceutical or non-pharmaceutical elements, which can be administered through the device. For example, one or more treatment devices can be disposed to monitor the efficacy of the current pharmaceutical or non-pharmaceutical dosage for the patient 170.

For example, the treatment devices 150 can include one or more of the following:

A video shading/inverse-shading element 151*a* coupled to the lenses 120, disposed to reduce intensity of incoming light, either for total intensity or for selected frequencies, and either for an entire incoming image or for a portion thereof (such as a light flare or glare element). For example, the control element 160 can determine when an incoming image includes light that is overly intense, overly rapidly changing, overly complex, or includes frequencies unduly likely to trigger a migraine, and can reduce those effects by selective use of the video shading/inverse-shading element.

A polarization element 151*b*, such as on the lenses 120, disposed to block incoming light that is polarized in a selected direction, either for total intensity or for selected frequencies, for light reaching the patient's eye. For example, the control element 160 can determine when an incoming image includes light that is overly polarized, such as glare or reflection, and can reduce the effects of overly polarized light by applying a linear polarization filter (such as found in polarized sunglasses).

As described herein, the control element 160 can direct the video shading/inverse-shading element 151*a*, the polarization element 151*b*, or both, to operate with the lenses 120, to reduce the effect of changes in lighting conditions and to reduce glare. This can have the effect one or more useful effects:

The patient 170 can be protected from a migraine caused by the change in lighting or by glare. This can include reducing the likelihood of migraine onset, reducing the severity or duration of a migraine, or reducing the duration or effect of a post-migraine ("postdrome") stage, or a combination of a migraine effect with photophobia.

The patient 170 can be protected from photophobia caused by the change in lighting or by glare. This can include reducing the likelihood of photophobia, or reducing the severity or duration of photophobia, or a combination of photophobia with a migraine effect.

The patient 170 can be protected from any negative effects when engaged in a sport activity, other outdoor activity, or an indoor activity in which light conditions are variable. As described herein, undesired effects can include reduced visibility, distraction, or otherwise.

As described herein, the video shading/inverse-shading element 151*a*, the polarization element 151*b*, or both together, can be applied in advance by the control element 160 when the latter predicts that the amount of light, or the amount of polarized light, will exceed a recommended threshold. The video shading/inverse-shading element 151*a*, the polarization element 151*b*, or both together, can also be applied at a time when the control element 160 measures that the amount of light, or the amount of polarized light, exceeds the recommended threshold. The recommended threshold for predicted light levels and for current light levels can differ, and can be responsive to a current condition of the patient 170, whether measured by the patient sensors 130, the ambient sensors 140, one or more reports from the patient 170, or otherwise.

As described herein, the recommended threshold can include a first selected threshold beyond which the likelihood of migraine offset is determined to be undesirable, a second selected threshold beyond which the likelihood of pain from photophobia is determined to be undesirable, or a combination thereof. As described herein, the first selected threshold and the second selected threshold can be responsive to one or more data repositories 420, treatment servers 430, or a combination thereof.

As described herein, the amount of light (or polarized light) determined to be excessive can be limited to particular ranges of frequencies, such as blue light or ultraviolet light. In addition to using the video shading/inverse-shading element 151*a*, the control element 160 can also use the light injection element 151*c* (as described herein), the frequency conversion crystal array 151*d* (as described herein), or a combination thereof, to adjust a balance of frequencies or a mix of frequencies to one better suited to the patient 170. For example, the control element 160 can use the video shading/inverse-shading element 151*a* to apply inverse shading to increase a relative amount of green light, or can use the light injection element 151*c* to inject green light to increase its amount relative to other frequencies, or a combination thereof. The recommended thresholds (whether distinct for predicted or actual incoming light, and whether distinct for migraine effects or photophobia) for each particular frequency can differ, and can be responsive to a current condition of the patient 170, whether measured by the patient sensors 130, the ambient sensors 140, one or more reports from the patient 170, or otherwise.

As described herein, the amount of light (or polarized light) determined to be excessive can be measured from a particular direction, such as in a peripheral vision direction. The control element 160 can separately measure the amount of light (or polarized light) entering the peripheral vision of the patient's eye, and can separately determine whether that amount of light (or polarized light) exceeds a recommended threshold. The recommended thresholds (whether distinct for predicted or actual incoming light, and whether distinct for migraine effects or photophobia, and whether distinct for any particular range of frequencies) for peripheral vision (and for distinct angles of peripheral vision, including side to side and up/down) can differ, and can be responsive to a current condition of the patient 170, whether measured by the patient sensors 130, the ambient sensors 140, one or more reports from the patient 170, or otherwise.

As described herein, the control element 160 can direct the video shading/inverse-shading element 151*a*, the polarization element 151*b*, the light injection element 151*c*, the frequency conversion crystal array 151*d*, or one or more combinations thereof, in response to a sport activity, other outdoor activity, or an indoor activity in which light conditions are variable. The control element 160 can direct the operation of these devices in combination with the lenses 120 in response to the type of activity, in response to the patient sensors 130, the ambient sensors 140, one or more reports from the patient 170 (such as the patient's movements to input data into the digital eyewear 100 using touch, using finger or hand movements within a field of view, using voice commands, using eye or head movements, or otherwise), or combinations thereof.

A light injection element 151*c* coupled to the lenses 120, disposed to inject light at frequencies known to be correlated with reducing the likelihood of a migraine, or with reducing the effect of a migraine that is occurring. For example, researchers have found that light in the green (520-560 nm) color range can have a positive effect for migraine patients 170. The control element 160 can determine when a migraine is likely or ongoing, and can administer treatment of this type.

In one embodiment, the control element 160 can be disposed to direct the light injection element 151*c* to inject green light into the eye to reduce the effects of migraines, and possibly of other headaches. In such cases, when the control element 160 determines that migraine activity is about to occur, or is currently occurring, the control element 160 directs the light injection element 151*c* to inject green light into the eye. For some patients 170, green light can have the effect of reducing the likelihood of an oncoming migraine, or when migraine activity is already occurring, can have the effect of reducing the severity of the migraine.

Alternatively, the control element 160 can be disposed to direct the video shading/inverse-shading element 151a, or the polarization element 151b, to reduce the intensity of colors other than green. This can have an effect similar to injecting green light into the patient's eye. The control element 160 can also be disposed to combine these effects, adding green light to selected portions of the incoming image and reducing non-green light from other selected portions of the incoming image. For example, the control element 160 can also be disposed to maintain the lens 120 at a relatively static state of increased amount of green, with reductions in non-green portions of the image where excess green would brighten the incoming image too much.

In other cases, when the control element 160 determines that the patient 170 is sleepy in the morning, or is otherwise sleepy at an abnormal time, the control element 160 can direct the light injection element 151c (after warning and obtaining approval from the patient 170) to inject blue light into the eye. For some patients, blue light can have the effect of waking the patient 170, or of reducing drowsiness or sleepiness for the patient 170. Similar to the description above with respect to green, the control element 160 can combine light injection with both shading/inverse-shading and polarization, and can reduce non-blue colors in portions of the image that would be made too bright by addition of excess blue.

As described herein, the control element 160 can direct the light injection element 151c, the frequency conversion crystal array 151d, or a combination thereof, to adjust a balance of light frequencies or a mix of light frequencies, to reduce the likelihood or severity/duration of migraines, to reduce the likelihood or severity/duration of photophobia, to reduce any negative effects when performing a sport or other activity in a changing environment, or a combination thereof.

- A frequency conversion crystal array 151d disposed to receive incoming light from an image upon which the eyes are focused, and to convert their photons from a first incoming frequency to a second presentation frequency. This can have the effect that the first frequency in the incoming light can be converted to the second frequency in the image presented to the patient 170. The control element 160 can be disposed to determine the first and second frequencies, and to determine for which portions of the image, or all of it, the frequency conversion is applied.
- An audio shading/inverse-shading element 151e, disposed to reduce intensity of incoming sound (such as one or more sharp rises of audio amplitude, or one or more selected audio frequencies), either for total intensity or for selected frequencies, and either for an entire set of incoming sounds or for a portion thereof (such as a screeching noise, or an element in the soundscape that is emitting any annoying noises, or the elements in the soundscape other than persons). For example, the control element 160 can determine when an incoming image includes sound that is overly intense, overly rapidly changing, overly complex, or includes frequencies unduly likely to trigger a migraine, and can reduce those effects by selective use of the audio shading/inverse-shading element.
- A sound or other sensory injection element 151f, disposed to inject sound or other senses known to be correlated with reducing the likelihood of a migraine, or with reducing the effect of a migraine that is occurring. For example, researchers have found that when the patient 170 relaxes, or is under less stress, a migraine is less likely to occur, and that migraine effects are better handled. When possible, the control element 160 can determine when a migraine is likely or ongoing, and can administer soothing sounds (such as music, nature sounds, or otherwise), relaxing smells or textures, or other treatment of this type.
- A medication induction element 151g, disposed to induce medication (such as using cutaneous medication, controlled release of implanted medication, or directions to the patient 170 to take medication in pill or liquid form) to reduce the likelihood of a migraine, or to reduce the effect of a migraine that is occurring. For example, the medication induction element 151g can operate under control of the control element 160 upon obtaining consent from the patient 170. For example, the medication can include pain relief medication (e.g., aspirin or ibuprofen) or other medications known to affect migraines (e.g., medications described herein with respect to migraines).
- A moisturizer induction element 151h, disposed to induce moisturizer, such as by aerosol applied to the eyes or the skin, to reduce the likelihood of a migraine, or to reduce the effect of a migraine that is occurring. For example, the moisturizer induction element 151h can operate under control of the control element 160 upon notifying the patient 170 (such as with a light buzzing sound). For example, the moisturizer can include saline for the eyes, or can include additional compounds for the skin.

In one embodiment, the moisturizer induction element 151h can be triggered, not just for migraines, but also for dry eyes or for eyestrain (such as can occur when the patient 170 has been concentrating on a television, computer screen, or mobile device screen, for an excessive amount of time). For example, the control element 160 can identify when the patient 170 has been focused on a television, computer screen, or mobile device screen, by noting that the patient's gaze direction or focal length has not changed much in some time, and that the patient 170 has received a much greater than normal amount of blue light. For another example, the control element 160 can determine what the patient 170 is looking at by using an outward-facing camera directed to an external image view. As described herein, maintaining a very short focal length (approximately <24 inches) for long durations can be damaging to the eye muscles. As a form of treatment, the control element 160 can direct the patient 170 to move their focus to a different (usually more distant) gaze direction or focal length, to rest the eye muscles and to allow the blink rate to recover, such as by looking out a window or otherwise at a relatively distant scene.

- A transcutaneous supraorbital nerve stimulation (t-SNS) device 151i, or similar device, coupled to the patient's nervous system, and disposed to introduce t-SNS treatment to reduce the likelihood of migraine onset. For example, the control element 160, when it determines that likelihood of migraine onset is relatively high, can obtain consent from the patient 170 and initiate this therapy.

FIG. 2

FIG. 2 (collectively including panels A, B, C, D, and E) shows a conceptual drawing of some alternative embodiments of the digital eyewear.

In alternative embodiments, the digital eyewear 100 can include one or more of the following:
  removable/replaceable, or otherwise augmentable, lenses 120;
  contact lenses 120 applied to a surface of the eye;

wearable/implantable lenses 120 implanted into a subsurface region of the eye;

one or more retinal image displays, which can be disposed to present images to selected portions of the retina;

one or more optic nerve stimulators, which can be disposed to stimulate selected portions of the optic nerve, which can have the effect of presenting the brain with selected images.

Removable/Replaceable Lenses

In one embodiment, shown in FIG. 2 panel A, the removable/replaceable lenses 120 can include a lens assembly coupled to the eyewear frame 110. The eyewear frame 110 can include a receptacle 111 disposed to fit the removable/replaceable lenses 120. In such cases, the removable/replaceable lenses 120 can be inserted into, or attached to, the receptacle 111, which can have the effect that the digital eyewear has its lenses 120 replaced with new lenses 120.

Contact Lenses

In one embodiment, shown in FIG. 2 panel B, the digital eyewear 100 can include contact lenses 120, which can include one or more lenses 120 applied to a surface of the eye, such as so-called "hard" and "soft" contact lenses, and including one or more elements of the lenses 120, as described herein, disposed in the contact lenses 120. For example, the lenses 120 can include one or more layers, such as a first layer 310 which can include an anti-reflective coating 311 and which can include an optical filtering element 312, and a second layer 320 which can include an anti-reflective coating 321 and can include an optical filtering element 322 (shown in FIG. 3).

For example, the contact lenses 120 can include one or more control circuits 330, which can be embedded in either the first layer 310, the second layer 320, or both, or otherwise embedded in the contact lenses 120. The control circuits 330 can be disposed outside the viewing area of the eye, such as in a location not overlapping the pupil or iris. The control circuits 330 can be disposed to receive control signals by wireless means, such as in response to an antenna 331, and can be disposed to control the optical filtering elements 312 and 322 in response to those control signals.

Wearable/Implantable Lenses

In one embodiment, shown in FIG. 2 panel C, the digital eyewear 100 can include wearable/implantable lenses 120 implanted into a subsurface region of the eye. For example, the natural lenses of the patient's eyes can be surgically replaced with wearable/implantable lenses 120. The lenses 120 can include one or more layers, such as a first layer 310 which can include an anti-reflective coating 311 and which can include an optical filtering element 312, and a second layer 320 which can include an optical filtering element 322 (shown in FIG. 3). The anti-reflective coating 321 at the rear of the second layer 320 might be unnecessary, as a retinal image display might not be directed to the rear of the second layer 320.

Retinal Image Display

In one embodiment, shown in FIG. 2 panel D, the digital eyewear 100 can include one or more retinal image displays (RID), laser and other external lighting images, "heads-up" displays (HUD), holographic displays, or other devices disposed to present an artificial image to the patient's eye (herein sometimes called an "artificial image display").

For example, an artificial image display can include a device disposed to emit light or other electromagnetic radiation into one or more selected portions of the retina. The selected portions of the retina can include (1) a location on the retina at which the eye is focusing external light, (2) a location on the retina near where the eye is focusing external light, but not in a direct focus region, (3) a location on the retina away from where the eye is focusing external light, or a combination or conjunction thereof. This can have the effect that the artificial image display can affect the patient's vision by directing light onto the retina, or can affect the patient's peripheral vision by directing light onto a location on the retina not in a direct focus region, or can affect the patient's brain state by directing light onto a location on the retina away from where the eye is focusing external light.

For example, the selected portions of the retina can include (1) a set of cones or cone receptors on the retina, which are sensitive to light of a selected frequency or frequency band, such as green light, or (2) a set of rods or rod receptors on the retina, which are sensitive to a total luminosity of light, such as a measure of brightness, or a combination or conjunction thereof. This can have the effect that the artificial image display can affect the patient's vision by directing light onto the retina to stimulate a color response from the patient 170, such as a response to green light. This can also have the effect that the artificial image display can affect the patient's vision by directing light onto the retina to stimulate a luminosity response from the patient 170, such as a response to relatively dark sunrise/sunset levels of light.

Optic Nerve Stimulator

In one embodiment, shown in FIG. 2 panel E, the digital eyewear 100 can include one or more optic nerve stimulators, disposed to directly stimulate the patient's optic nerve. For example, the optic nerve stimulators can be disposed to stimulate nerve cells in the optic nerve using electronic signals applied directly to those nerve cells, using light applied directly to those nerve cells, or using electromagnetic signals applied indirectly to those nerve cells (such as from outside the patient's skull).

For example, the optic nerve stimulators can be disposed to stimulate/inhibit the optic nerve, with the effect that the patient's eye transmits relatively more or relatively less information to the brain. Excess brain stimulation can be correlated with migraine activity, so it can occur that reducing transmitted information to the brain can reduce the likelihood of migraine onset, or alleviate or shorted the duration of migraine activity.

FIG. 3

FIG. 3 shows a conceptual drawing of a system including digital eyewear with controllable lenses.

As described herein, the lenses 120 can include multiple digital lenses, multi-layered lenses or multi-coated lenses, such as the first layer 310 and the second layer 320, as described herein.

First Layer

In one embodiment, the first layer 310 can include an outer layer (at its front portion), having an anti-reflective coating 311, and can include an optical filtering element 312. As described herein, the anti-reflective coating 311 can provide an anti-reflective effect; the antireflective effect can be responsive to selected frequencies of incoming electromagnetic radiation. For example, the anti-reflective coating 311 can be disposed to reduce particular selected electromagnetic frequencies or frequency bands, such as: blue light, ultraviolet A radiation, ultraviolet B radiation, or otherwise.

As described herein, the optical filtering element 312 can be disposed to differentially filter electromagnetic radiation in response to frequencies or frequency bands. The optical filtering element 312 can be disposed to be either static or electrodynamic. When the optical filtering element 312 is static, it has a substantially constant filtering effect, at each time, at each of its locations.

When the optical filtering element 312 is electrodynamic, it can receive one or more control signals 313a, 313b, and the like, specifying individual locations of selected areas 314 of the optical filtering element 312, and for what frequencies those selected areas 314 are filtered. The selected areas 314 can include individual pixels, or small groups thereof, to be distinctly filtered by the optical filtering element 312. The control signals 313a, 313b, and the like, can select areas 314 in a time sliced manner, allocating a relatively small time to each one.

This can have the effect that shading/inverse-shading can be performed individually and distinctly for each selected area 314, that is, that each selected area 314 can have its own electrochromatic effect specified for each moment in time. This can have the effect that the control element 160 can, say, choose a selected area 314 to reduce the amount of blue light it allows through in a first time slice, and to increase the amount of green light it allows through in a second time slice. When each time slice is small enough, the eye should be substantially unable to identify the separate filtering operations, so that both are collectively perceived as being performed concurrently.

Second Layer

In one embodiment, similarly, the second layer 320 can include an outer layer (at its rear portion), having an anti-reflective coating 321, and can include an optical filtering element 322. As shown in the figure, the second layer 320 can be disposed nearer the eye, with a retinal image display coupled to reflect images from the rear portion of the second layer 320 (nearer the eye), into the eye.

Similarly to the first layer 310, the second layer's anti-reflective coating 321 can provide an anti-reflective effect; the anti-reflective effect can be responsive to selected frequencies of incoming electromagnetic radiation. Also similarly to the first layer 310, the second layer's optical filtering element 322 can be either static or electrodynamic; when electrodynamic, the second layer's optical filtering element 322 can be responsive to control signals 323a, 323b, and the like, to specify individual locations of selected areas 324 of the optical filtering element 322, and for what frequencies those selected areas 324 are filtered.

As described herein, the first layer 310 can be shaded/inverse-shaded electrodynamically with respect to particular frequencies or frequency bands, while the second layer 320 can be shaded/inverse-shaded electrodynamically for luminosity (thus, all frequencies at once, with a monochrome shading/inverse-shading effect).

Combination

In one embodiment, one of the two layers can include a fast-acting adaptive shading element and can be disposed for relatively rapid control of light intensity, while the other one of the two layers can include an adaptive electrochromatic effect that selects between (1) a clear state, or (2) in a filtering state to shade/inverse-shade selected frequencies or frequency bands. A combination or conjunction of the two layers can have the effect of rapid reaction to changes in light intensity, while also adapting to a chromatic balance of an image available to the user.

Visual Effects

The lenses 120 can be coupled to a controlling device accessible by the digital eyewear 100, such as the control element 160, to control one or more visual effects to be presented to the patient. The visual effects can include one or more of:

shading/inverse-shading, such as reducing or increasing the luminosity or polarization of one or more pixels of an image presented to the patient. In one embodiment, shading/inverse-shading can be provided by one or more of: the video shading/inverse-shading element 151a, the polarization element 151b, the light injection element 151c.

color shading/inverse-shading, such as reducing or increasing the intensity of one or more colors (or other frequencies, such as ultraviolet) in an image presented to the patient. In one embodiment, color shading/inverse-shading can be provided by one or more of: the video shading/inverse-shading element 151a, the polarization element 151b, the light injection element 151c, as applied to particular sets of colors (or other frequencies, such as ultraviolet), or the frequency conversion crystal array 151d.

One or more of the visual effects can be controlled by the controlling device accessible by the digital eyewear 100, such as the control element 160. This can have the effect that the visual effects are responsive to one or more of: optical/perceptual parameters, parameters personalized to the patient 170, or the patient's mental state. The optical/perceptual parameters can include values derived from one or more of the patient sensors 130, the ambient sensors 140, or feedback from the treatment devices 150. For example, the optical/perceptual parameters, the parameters personalized to the patient 170, or the patient's mental state, can be derived by the control element 160 from dynamic eye tracking, such as in response to the gaze direction and focal length sensor 132b, the pupillometry sensor 132a, or other patient sensors 130.

For example, the pupillometry sensor 132a can be coupled to a shading/inverse-shading device, to provide shading/inverse-shading in response to the patient's eye. When the pupillometry sensor 132a detects dilated pupils, such as might occur in low ambient light conditions, the control element 160 can adjust shading/inverse-shading to increase luminosity. Similarly, when the pupillometry sensor 132a detects constricted pupils, such as might occur in high ambient light conditions (or light conditions including bright lighting, glare, having the sun in view, or otherwise), the control element 160 can adjust shading/inverse-shading to decrease luminosity. The reduced or increased luminosity can be applied to:

an entire image.

a portion of the image at which the patient 170 is looking, such as in response to gaze direction;

a specific region in three-dimensional (3D) space on which the patient's eye is focused, such as in response to gaze direction and focal length;

a specific object at which the patient 170 is looking, such as in response to object recognition, facial recognition, or prediction in response to context;

For example, if the patient's focal length remains relatively constant at a selected distance such as about 24 inches, the digital eyewear 100 can determine that the patient is staring at a computer screen. For another example, if the patient 170 is receiving audio input interpretable as speech, the control element 160 can determine that the patient 170 is likely looking at the person originating that speech; in such cases, the control element 160 can shade/inverse-shade a portion of the image for a view by the patient 170 of the person originating that speech.

a specific object at which the digital eyewear 100 determines the patient 170 should be looking, such as in response to a prediction or assessment with respect to migraines;

a message that the digital eyewear 100 presents to the patient 170, such as a directive or suggestion with respect to the treatment devices 160 or with respect to self-care;

a message that the digital eyewear 100 receives for the patient 170, such as an incoming message from a distinct digital eyewear 100, or from another messaging device such as a mobile telephone, or such as an informative message or an advertisement. The informative message can be one or more of: a public alert or a public service message (such as an "Amber Alert", a weather alert, or other warning), a message localized to a particular location or region (such as a danger warning sign, local map, road sign, or otherwise).

In such cases, the patient sensors 130, including one or more of the pupillometry sensor 132*a*, or the gaze direction and focal length sensor 132*b*, can be coupled to the control element 160. The control element 160 can determine a three-dimensional (3D) location or region with respect to which the patient's attention is focused. The control element 160 can receive audio/video input from that location or region, and perform object recognition, facial recognition, or other statistical assessment of the audio/video input. The control element 160 can control one or more audio/visual effects to be applied to the audio/video input before that input is presented to the patient. For example, in a relatively noisy environment, the control element 160 can shade audio signals other than the source of the focused-upon audio, and inverse-shade audio signals from the source of the focused-upon audio, thus improving reception of the focused-upon audio. The control element 160 can perform shading/inverse-shading, color shading/inverse-shading, color frequencies transformations, false-coloring (to either or both of audio/video frequencies), and other alterations to the audio/video input before that input is presented to the patient, as described herein.

For another example, the patient's optical/perceptual parameters can be responsive to one or more of the patient sensors 130. In such cases, the optical/perceptual parameters can be derived from one or more of:

measurements of optical expression: including whether the patient's eyes are open/closed, blink rate, whether the patient's pupils are wide/narrow, whether the patient is squinting, the patient's rate of eye saccades, and otherwise;

measurements of the patient's voice: including voice commands, frequency measurements of the patient's voice, audio volume, and otherwise;

measurements of the patient's brainwaves, including measurements in response to an EEG, fMRI, or other brain activity measurement device;

measurements of the patient's environmental conditions: including responsive to one or more ambient sensors 140;

and other determinations with respect to the patient's audio, video, navigational, augmented reality, algorithmic, spatial, cognitive, interpretive, or other features.

As described in the Incorporated Disclosures:

The shading control can be provided by one or more projectors within the wearable optics device. An occlusion effect can be projected on a lens of the wearable optics device. The shading can be provided on a lens of the wearable optics device wherein the surrounding area is occluded or reversed. The shading is provided by a polarized filter. The shading control can be provided by the lenses within the wearable optics device. The shading can be controlled using optical parameters. The optical parameters include any or any combination of ciliary, pupil, corneal, lens, iris, eyelid, and retina measurements. Materials that can electrically control any or any combination of chromatic, refractive, diffractive, transparent, reflective properties of the wearable optics device are utilized with the dynamic eye tracking. The lens can be any or any combination of transparent LCD, LED, OLED, flexible LED, flexible OLED, transparent matrix, semi-transparent matrix, prism based, holographic, electroluminescence, eletroreflective, dynamic filtering materials.

The wearable optics device comprises an electrochromatic material. In a system and method in accordance with an embodiment one or more elements are utilized within the wearable optics device to provide image information into the eye. The one or more elements include any or any combination of a lens projector, retinal projection. The retinal projection or projector plus prism provide the occlusion.

The wearable optics device includes shading control for the eyewear. In the wearable optics device, portions of an image viewed by the wearable optics device can be shaded to control brightness. The lenses of the wearable optics device can be controlled polarizing, transparent OLED, or projection and prism lenses.

The parameters may include any or any combination of prescriptions for improving the vision of a user, a zoom feature, a microscope feature, magnifying feature, retinal projection feature. The wearable optics device can be utilized in a simulator. In an embodiment, a focal of the wearable optics device is utilized in conjunction with the dynamic eye tracking.

The parameters can include any or any combination of a zoom feature, a microscope feature, magnifying feature, illumination feature; a retinal projection feature. In an embodiment a 360 degree view can be provided. The 360 degree view can be any or any combination of a left or right panning, up and down panning, three dimensional rotations.

In another embodiment, an illumination feature is directed to a specific area based upon the dynamic eye tracking mechanism. A wearable optics device camera feature can filter certain light waves for controlled viewing or visual effects. The filtering feature can include controlling noise reduction, polarization, and creative effects. The wearable optics device feature can include controlling a stability control for facial or object focus. In an embodiment optical parameters can be utilized. The optical parameters include any of or any combination of ciliary, pupil, corneal, retina, lens, iris measurements. An embodiment may include detecting head movement. An acoustic wave mechanism may be utilized within the wearable optics device. A brain wave mechanism may be utilized within the wearable optics device. A magnetic wave mechanism may be utilized within the wearable optics device.

For another example, the patient's mental state, such as one or more emotions, can be derived from similar elements as those used to predict or assess migraine activity, as described herein. In such cases, the elements used to predict or assess migraine activity can be similarly used, using similar methods to those described herein with respect to migraine activity, to predict or assess particular patient emotions. In such cases, the patient emotions to be predicted or assessed can include common emotional states, such as one or more of: anger, disgust, fear, joy, sadness, surprise, and otherwise.

Predictive Visual Effects

The digital eyewear 100 can predict and assess expected upcoming optical/perceptual parameters, parameters personalized to the patient 170, or patient mental state. In one embodiment, the control element 160 of the digital eyewear 100 can determine, in response to patient sensors 130 and ambient sensors 140, one or more activities with respect to which the patient 170 is engaged. In response thereto, the control element 160 can determine a predictive assessment of one or more likely upcoming inputs from patient sensors 130 and ambient sensors 140.

For example, when the patient 170 is looking at a computer screen, the control element 160 can predict a measure of incoming luminance for each one of a set of frequencies, including blue light and ultraviolet light. In such cases, the control element 160 can predict a measure of incoming video and audio noise, and in response to the patient sensors 130, a measure of expected upcoming patient activation. Patient "activation" can include increases/decreases in one or more of: likelihood of patient migraine onset or continuation, patient audio/video mental responses, patient responses including eye/head movement or emotions, or other patient responses.

FIG. 4

FIG. 4 shows a conceptual drawing of a system including digital eyewear communication.

The system can be described herein with respect to elements shown in the figures, such as:
- the digital eyewear 100;
- the control element 160, including its computing device 161 and one or more communicators 162 and their sending/receiving elements;
- one or more communication links 210;
- one or more data repositories 420;
- one or more treatment servers 430, such as computing servers disposed to determine more complex assessments of migraine likelihood and seriousness, and such as medical personnel or others disposed to assist the patient 170.

The control element 160 for the digital eyewear 100 can be coupled, under control of its computing device 161 and using its communicators 162, to the communication links 210. The communication links 210 can be coupled to a communication network such as the internet, by which they can access one or more of the data repositories 420 or treatment servers 430.

As described herein, the digital eyewear 100 can perform its operations in response to a collective database, such as a collective database that is remotely maintained and is updated with respect to patient information with respect to migraines. For example, each instance of digital eyewear 100, that is, digital eyewear 100 for each patient, can report its information to the data repositories 420 and treatment servers 430, with the effect that the data repositories 420 and treatment servers 430 can maintain collective data with respect to patients and their possible migraines.

Collective data can also include information injected into data repositories 420 by known data sources, such as weather reports, pollution control reports, and allergen reports. For example, known data sources can associate information with respect to weather (e.g., current and predicted weather conditions), pollution (e.g., current and predicted air pollution levels), and allergens (e.g., current and predicted pollen counts), and can deliver that information to digital eyewear 100 in response to GPS location information. This can have the effect that each instance of digital eyewear 100 does not need to independently measure weather, pollution, or allergens, and does not need to attempt to predict future conditions thereof.

As described herein, the digital eyewear 100 can also perform its operations in coordination with other instances of digital eyewear 100, such as for example coordinating action to ameliorate or treat migraines in response to nearby patients 170 and their migraine activity. For example, when a first instance of digital eyewear 100 reports a substantial disturbance that might have an emotional effect on a patient 170 using a second instance of digital eyewear 100, the first digital eyewear 100 can inform the second digital eyewear 100 thereof. The first digital eyewear 100 can communicate with the second digital eyewear 100 under control of their computing devices 161 and using their communicators 162.

For another example, when a first patient 170 using a first instance of digital eyewear 100 and a second patient 170 using a second instance of digital eyewear 100 are participating in a joint activity, the first instance of digital eyewear 100 can inform the second instance of digital eyewear 100 of any changes in light conditions that affect the first patient 170 and that might affect the second patient 170. In such cases, the first instance of digital eyewear 100 can also inform the second instance of digital eyewear 100 of any alterations to light effects that the first instance of digital eyewear 100 decided to apply, so that the first patient 170 was not negatively affected thereby. The second instance of digital eyewear 100 can choose to apply similar alterations to light effects, so that the second patient 170 is not negatively affected thereby.

In one such case, a removal of cloud cover might cause a sudden brightening of an environment where the first patient 170 and the second patient 170 are performing an activity. While this Application primarily describes cases in which removal of cloud cover might affect an outside activity, in the context of the invention, there is no particular requirement for any such limitation. For example, removal of cloud cover can affect light through a window. Alternatively, sudden imposition of cloud cover might cause sudden darkening, or a bright light might be switched on or off. The sudden brightening/darkening can be detected by the first instance of digital eyewear 100, which can inform the second instance of digital eyewear 100 without the latter having to make the same determination for itself. Similar procedures can apply for application of a particular range of frequencies, or for glare, or otherwise.

Alternatively, when the first patient 170 and the second patient 170 are not similarly situated, such as when the first patient 170 and the second patient 170 have differing reactivity to light regarding migraine effects or photophobia, the first instance of digital eyewear 100 and the second instance of digital eyewear 100 can determine to take differing steps in response to changes in the light environment. For example, when the first patient 170 is more sensitive than the second patient 170 to migraine effects or photophobia, the first instance of digital eyewear 100 can take more aggressive action than the second instance of digital eyewear 100, to reduce the likelihood or severity/duration of migraine effects or photophobia.

FIG. 5

FIG. 5 shows a conceptual drawing of a method including operation of digital eyewear.

A method 500 includes flow points and method steps as described herein.

Although these flow points and method steps are (by the nature of the written word) described in a particular order, in the context of the invention there is no particular requirement for any particular order. This description does not limit the method to this particular order. They might be performed in a different order, or concurrently, or partially concurrently, or otherwise in a parallel, pipelined, quasi-parallel, or other manner. They might be performed in part, paused, and returned to for completion. They might be performed as co-routines or otherwise.

One or more portions of the method 500 are sometimes described as being performed by particular elements of the system described with respect to FIG. 1 and FIG. 2, or sometimes by "the method" itself. When a flow point or method step is described as being performed by "the method," it can be performed by one or more of those elements, by one or more portions of those elements, by an element not described with respect to the figure, by a combination or conjunction thereof, or otherwise.

Beginning of Method

A flow point 500A indicates a beginning of the method.

The digital eyewear 100 (shown in FIG. 1) performs operations for monitoring, detecting, and predicting migraines, for preventing migraines, for treating migraines, and for training patients 170 to conduct self-care with respect to migraines. These operations can be performed in real-time. Similarly, the digital eyewear 100 performs operations for monitoring, detecting, and predicting photophobia effects, for preventing photophobia effects, for treating photophobia effects, and for training patients 170 to conduct self-care with respect to photophobia effects. Similarly, the digital eyewear 100 performs operations for monitoring, detecting, and predicting negative sensory (whether visual, auditory, or otherwise) effects from changing ambient conditions, for preventing negative sensory effects from changing ambient conditions, and for treating negative sensory effects from changing ambient conditions.

The digital eyewear 100 can be disposed to receive information from patient sensors and ambient sensors, to maintain a history of patient migraine activity (and photophobia effects) and any ameliorative or treatment activity thereof, either locally or at a data repository 420 (shown in FIG. 2), to determine one or more correlations between sensor data and either migraine effects or photophobia effects, either locally or at a treatment server 430 (shown in FIG. 2), to predict and treat migraines or photophobia effects (possibly with the assistance of a treatment server 430), and to conduct patient training.

Monitoring Patient Reactions

At a flow point 510, the digital eyewear 100 (shown in FIG. 1) is ready to monitor patient sensors 130 and ambient sensors 140.

At a step 511, the digital eyewear 100 receives direct information from the patient sensors 130 and ambient sensors 140. The control system 160 can determine derivative information with respect to that direct information, such as at least first and second time-derivatives thereof, at least first and second statistical moments thereof, and such as correlations between that information and any other information available to the digital eyewear 100. For example, as described herein, the control system 160 can determine correlations between that information and patient self-reports of migraine effects or photophobia effects, possibly with the assistance of one or more treatment servers 430 (shown in FIG. 2).

At a step 512, the digital eyewear 100 collects a set of history information from the patient sensors 130 and ambient sensors 140, the treatment devices 150, and patient self-reports of migraine effects or photophobia effects. As noted with respect to the just-previous step, the control system 160 can determine correlations using that history information.

At a step 513, the digital eyewear 100 exchanges the history information with one or more data repositories 420 and treatment servers 430. In one embodiment, medical personnel, such as at a neurologist's office, can determine a set of baseline information, or the patient 170 can collect information independently for a period of time.

In one embodiment, the patient can self-report on migraines or photophobia effects by using an input device on the digital eyewear 100, or by using a smartphone app on a mobile device (not shown) that is coupled to one of the communicators 162 on the digital eyewear 100. For example, the digital eyewear 100 can include one or more buttons by which the patient 170 can provide input to the digital eyewear 100. For another example, the patient 170 can use eye gaze and eye movement to interact with an augmented reality view provided by the digital eyewear 100. For another example, the patient 170 can use hand or limb movement to interact with a external-facing camera available to the digital eyewear 100, with the effect that the digital eyewear 100 can detect patient signals indicating migraine effects. For another example, the digital eyewear 100 can receive patient verbalization about migraine effects, which it can transcribe into information or which it can send to a treatment server 430 for transcription into information.

Patient input can be patient-initiated or can be in response to a request for information from the digital eyewear 100.

As part of this step, the digital eyewear 100 can use its communicator 162 to exchange messages with a smartphone app on a mobile device, such as to obtain information from the patient 170. For example, the smartphone app can ask the patient 170 to describe their symptoms, to identify where they have pain, to identify the nature and severity of the pain (such as: sharp versus throbbing, where localized, mild or painful or very painful or debilitating), to identify any current emotions or other stressors, to identify who or what is present near them, to identify whether they perceive an "aura" and its nature, to identify what medications they have taken, to identify what they were doing beforehand, to request whether they would like an emergency response, and possibly other questions.

As part of this step, the digital eyewear 100 can use its communicator 162 to exchange other and further messages with a smartphone app on a mobile device, such as to obtain information from the smartphone that the patient 170 has entered in the past. In one embodiment, the patient 170 can maintain a "migraine diary" or a "photophobia diary" using the smartphone app, similar to current migraine diaries maintained on paper, except that the digital eyewear 100 can obtain information from the online migraine diary or photophobia diary for use as history information with respect to the patient's migraines or photophobia effects.

The method proceeds with the next flow point.

Detecting Migraines and/or Photophobia

At a flow point 520, the digital eyewear 100 is ready to determine migraine onset and to detect ongoing migraines. Similarly, the digital eyewear 100 is also ready to determine the beginning or continuation of photophobia effects.

At a step 521, the digital eyewear 100 can detect migraine activity or photophobia effects, either in response to patient input (as described herein), or in response to information from patient sensors 130.

In one embodiment, the digital eyewear 100 determines only a likelihood that migraine onset or migraine activity is occurring, or that photophobia effects are occurring, or a combination thereof. For example, the control element 160 can be responsive to a set of input parameters, and can determine from those input parameters a likelihood of whether a migraine is occurring (whether "pro-dome," "migraine," "aura," or "post-dome"), or whether a photophobia effect is occurring. In such cases, the control element 160 can give substantial weight to the patient's assessment of a migraine or a photophobia effect, but there is no special requirement to take the patient's assessment as conclusive. The patient 170 might have erroneously tapped an input button indicating a migraine or a photophobia effect, or the patient 170 might have inaccurately concluded that a severe headache was a migraine or a photophobia effect. Absent evidence otherwise, the control element 160 can use the patient's assessment as an indicator to adjust its own predictive parameters, as described herein.

For example, the digital eyewear 100 can determine a likelihood of migraine onset or the beginning of a photophobia effect, either in the near future, or in the case of a migraine, by recognition of the "prodome" portion of migraine activity. In such examples, the digital eyewear 100 can determine a measure of likelihood, such as either a numerical probability estimate, or a bucketed probability estimate of the form "very likely," "likely," "somewhat likely," or "relatively remote."

In one embodiment, the digital eyewear 100 can determine a likelihood of migraine onset, or the beginning of a photophobia effect, in response to visual input or light intensity. For example, sudden glare, rapidly flashing bright light, and lighting that changes with unstable frequency, can each be correlated with migraine onset.

In one embodiment, the control element 160 can be responsive to total light intensity, to total light intensity in the blue (approximately 450-490 nm) and ultraviolet (primarily <~300 nm) frequency ranges, and to total light intensity applied to selected regions of the retina. For example, the control element 160 can be responsive to total light intensity, or to total light intensity in selected frequency ranges, applied to specific portions of the retina, such as those portions of the retina including the cone receptors or those portions of the retina including the rod receptors. Similarly, the control element 160 can be responsive to total light intensity, or to total light intensity in selected frequency ranges, for light infalling on a peripheral vision portion of the retina.

For example, the control element 160 can be responsive to total light intensity (whether total intensity or in selected frequency ranges), or to light intensity (whether total intensity or in selected frequency ranges) infalling on specific portions of the retina (such as those portions of the retina including the cone receptors or those portions of the retina including the rod receptors, or such as those portions of the retina including a peripheral vision portion of the retina. In such cases, the control element 160 can be responsive to first and second time-derivatives, and to a frequency of modulation—such as a 60 Hz modulation for light bulbs, or an unstable frequency of modulation for other light sources. In such cases, the measurement can be (a) with respect to total light intensity, (b) with respect to total light intensity in the blue and ultraviolet frequency ranges, (c) with respect to total light intensity actually applied to specific portions of the retina. For another example, the control element 160 can also be responsive to derivative information thereof, such as at least first and second time-derivatives thereof, or at least first and second statistical moments thereof.

For another example, as described herein, the control element 160 can be responsive to a measurement of pupillary diameter (such as found by a pupillometry sensor 132*a*). In such cases, the control element 160 can be responsive to at least first and second time-derivatives thereof, to at least first and second statistical moments thereof, to a frequency of modulation, and to a match between right and left eye—such as whether the pupillary diameter itself changes suddenly, or vibrates, or is unstable. It is believed that unusual changes in pupillary diameter are correlated with migraine onset and migraine activity.

For another example, when 100 candela/square-meter is applied to the patient's eyes, it could occur that only the smaller amount of about 10 candela/square-meter, where the ratio from incoming light to the amount of light that actually reaches the retina is approximately $\pi r^2$ (where r is the pupillary diameter) and it could occur that an even smaller amount is applied to the patient's rods or cones. It could also occur that an even smaller amount is applied to the patient's retina in view of color filtering due to the iris. It could also occur that a smaller amount is applied to a peripheral vision portion of the patient's retina. In such cases, the control element 160 can be responsive to total EEG activity, which can be responsive to light excitation of the patient's retina, with the effect that total EEG activity, or pupillary diameter, or a combination thereof, can be used as a proxy for infalling light on the patient's rods or cones, or a proxy for selected frequencies of infalling light on the patient's rods or cones, or a proxy for infalling light on a peripheral vision portion of the patient's retina. In such cases, the control element 160 can also be responsive to at least first and second time-derivatives thereof, to at least first and second statistical moments thereof.

For another example, the control element 160 can be responsive to a complexity of an input image, or a rapidity or complexity with which the input image changes, or a rapidity or complexity with which a peripheral vision portion of the input image changes; this can be measured in response to a set of high-frequency components of a 2D Fourier transform of the input image, and in response to at least a first and second time-derivative thereof, or at least first and second statistical moments thereof.

In one embodiment, the digital eyewear 100 can determine a likelihood of migraine onset in response to audio input or sound intensity. For example, sudden loud noises can be correlated with migraine onset. For example, discordant notes and disturbing music can be correlated with migraine onset. For another example, similar to the responses to light described herein, the digital eyewear 100 can be responsive to total sound intensity, to sound intensity at selected frequencies (such a high-frequency whine), to sound intensity at discordant intervals (such as relative sound intensity at unusual frequency ratios or with painful beat frequencies, and to sound intensity with unusual time intervals (such as fifth notes or seventh notes, instead of quarter notes or half notes).

In one embodiment, the digital eyewear 100 can determine a current migraine event, such as an "attack" or "aura" portion of migraine activity, or a "post-dome" portion of migraine activity, or a current photophobia effect, such as a beginning or a continuation of an effect, or a winding down of a photophobia effect. For example, the control element 160 can determine a measure of seriousness of the migraine event or the photophobia effect, such as a measure of pain, or a measure of likelihood that the migraine or the photophobia effect will further develop into a more debilitating event, or a measure of likelihood that the migraine or the photophobia effect is indicative of a more serious medical trauma. For another example, the control element 160 can be responsive to similar sensors and to similar inputs from those sensors as when predicting migraine onset or the beginning of a photophobia effect. In such cases, the control element 160 can be additionally responsive to a measure of whether the patient's response to sensory inputs is increasing in intensity or discordancy/complexity, wherein the control element 160 can determine that the migraine activity or the photophobia effect is likely to be increasing in intensity.

At a step 522, in one embodiment, when the digital eyewear 100 determines that the migraine or the photophobia effect is sufficiently serious, the digital eyewear 100 can use its communicators 162 to obtain assistance from one or more treatment servers 430. For example, when the digital eyewear 100 determines that the patient 170 is seriously disabled, it can call for assistance. For another example, when the digital eyewear 100 determines that the patient 170 is disabled and is also currently operating heavy machinery (e.g., is driving an automobile), it can call for assistance. For another example, when the digital eyewear 100 determines that the patient 170 is at risk for a more serious medical trauma (such as a stroke or other brain trauma), it can call for assistance, possibly including a request for help from medical personnel or emergency responders.

At a step 523, the digital eyewear 100 maintains a record of the migraine onset likelihood or the migraine event, or similar information for photophobia effects, and reports that record to one or more data repositories 420.

The method proceeds with the next flow point.

Prediction of Migraines and/or Photophobia

At a flow point 530, the digital eyewear 100 is ready to predict migraine onset or ongoing migraines. Similarly, the digital eyewear 100 is ready to predict the beginning of photophobia effects or continuation of photophobia effects.

At a step 531, the digital eyewear 100 accesses the record of migraine onset likelihood and migraine events, or similar information with respect to photophobia effects, from one or more data repositories 420 and from the memory of its computing device 161.

At a step 532, the control element 160 assigns a set of weights to each sensor value it receives, such as from the patient sensors 130 and the ambient sensors 140. As the sensor values from many of the patient sensors 130 and the ambient sensors 140 are time varying, the digital eyewear 100 assigns one weighting value (or a time-varying function from which it can determine a weighting value) to each such time series. For example, the control element 160 can receive the set of weights, or the set of functions from which time varying weights are determined, from one or more data repositories 420 or from one or more treatment servers 430.

At a step 533, the control element 160 conducts an "adaptive tuning" (or "selftuning") technique to adjust the weights it has assigned to each sensor value (or the time varying weights it has assigned to each time varying sensor value). For example, the control element 160 can use an adaptive control technique to minimize error between the weighted determination of results (in response to sensor inputs) and the actual results (in response to actual measurement). In such cases, the control element 160 can be responsive to actual determination of migraine activity or photophobia effects to adjust its parameters for future prediction of migraine activity or photophobia effects from input sensors.

In one embodiment, the control element 160 can determine its prediction of likelihood of future migraine activity or photophobia effects in response to input sensors using a linear weighted model:

$$Pr_M(t) = SUM_i \omega_i(t) s_i(t)$$

where the sum is computed for all weights $\omega_i$ and all sensor values $s_i$ and where the value $SUM_i \omega_i(t) s_i(t)$ is a dot product for the sequence of time values In one embodiment, the control element 160 can compare its prediction $Pr_M(t)$ with the actual later determination of whether a migraine event or a photophobia effect actually occurred at time t. (In alternative embodiments, separate prediction parameters $\omega_i$ can be maintained for migraine prediction and for photophobia prediction.) Depending on whether the actual later determination is yes or no (that is, there was a migraine event or a photophobia effect or not), the control element 160 can adjust each of the assigned weights $\omega_i$ in response to its contribution to a measure of error, usually the square of the difference between $Pr_M(t)$ and the actual later determination. See Wikipedia (Self-tuning), en.wikipedia.org/wiki/Self-tuning, and Wikipedia (Adaptive control), en.wikipedia.org/wiki/Adaptive_control, and references cited therein, each of which is hereby incorporated by reference.

While this Application primarily describes use of adaptive tuning, in the context of the invention, there is no particular requirement for any such limitation. Any time series adjustment technique would be suitable, and could be used in the context described.

For example, the control element 160 could use an adaptive recursive model (in which each weight is adjusted by a fraction a of its contribution to the computed error). For another example, the control element 160 could use another measure of error, such as a Frobenius Norm with a parameter other than the Euclidean Norm. See Wolfram MathWorld (Frobenius Norm), mathworld.wolfram.com/Frobenius-Norm, and references cited therein, each of which is hereby incorporated by reference.

For another example, the control element 160 could use a recurrent neural network (RNN), to determine a sequence of parameters to apply to a set of time-delayed values of each sensor. The control element 160 can include a sequence of N hidden state values, each to be applied to one of the past N measured values, and each to be updated after a new measured value is seen. Thus, where $\omega_i$ represents a vector of weights for the past N measured values, $s_i$ represents the actual measured values, the ∘ operation represents a vector dot product, and the tan h function is separately applied to each element of the vector:

$$\omega^*_i = \omega_i \pm \tan h(\omega_i \circ s_i)$$

(where the ±function is applied as plus/minus in response to whether the prediction was accurate)

with the effect that new weights $\omega^*_i$ are adjusted in response to the old weights $\omega_i$ and the sensor values $s_i$, and $$Pr_M = \omega^*_i \circ s_i$$

with the effect that the computed probability is also a dot product of the sequence of time values The weight vector $\omega_i$ is repeatedly updated for each new sample, and the weight vector is adjusted positively whenever the result is "correct" (such as, $Pr_M >$ some threshold, e.g., 0.6, and the patient 170 reports a migraine or a photophobia effect; or $Pr_M <$ some other threshold, e.g., 0.4, and the patient 170 reports no migraine or photophobia effect), and adjusted negatively whenever the result is "incorrect" (such as, $Pr_M <$ some threshold, e.g., 0.4, and the patient 170 reports a migraine or a photophobia effect; or $Pr_M$>some other threshold, e.g., 0.6, and the patient 170 reports no migraine or photophobia effect), and where there is no adjustment for ambiguity (such as, $0.4<Pr_M<0.6$). In alternative embodiments, separate prediction parameters $\omega_i$ can be maintained for migraine prediction and for photophobia prediction.

After a relatively large number of sample sensor values $s_i$, the adjusted weights $\omega_i$ should accurately reflect a measure of likelihood that the patient 170 is about to have a migraine or a photophobia effect. The sensor values and weights can be determined separately for each patient 170, collectively for multiple patients, or independently in response to whether patients 170 have "chronic" migraines or not, or in response to other factors. See Wikipedia (Recurrent Neural Network), en.wikipedia.org/wiki/Recurrent_neural_network, and references cited therein, and A. Karpathy, "The Unreasonable Effectiveness of Recurrent Neural Networks", karpathy.github.io/2015/05/21/rnn-effectiveness/, and references cited therein, each of which is hereby incorporated by reference.

While this Application primarily describes, in the context of time-delayed values of each sensor, use of a recurrent neural network, in the context of the invention, there is no particular requirement for any such limitation. Any other machine learning (ML) technique would be suitable, and could be used in the context described. For example, the control element 160 could use a Kohonen Network or a Random Forest technique to separate the set of possible set of earlier time-delayed values into a set of clusters, each with its own set of predictive or evaluative parameters. See Wikipedia (Machine Learning), en.wikipedia.org/wiki/Machine_learning, and references cited therein, and Wikipedia (Artificial Intelligence), en.wikipedia.org/wiki/Artificial_intelligence, and references cited therein, each of which is hereby incorporated by reference.

This Application describes methods by which the digital eyewear 100 can predict migraines or photophobia effects. The digital eyewear 100 can determine, in a similar manner, whether the patient 170 actually has a current migraine or photophobia effect, whether a particular treatment will ameliorate the patient's migraine or photophobia effect, whether the migraine or photophobia effect will recur, whether a particular patient 170 will respond to a suggested method of patient self-care, and whether a particular patient 170 will respond to a particular method of reinforcing successful patient self-care (above and beyond the patient 170 having been reinforced by actual success of the self-care by avoidance or treatment of a migraine or photophobia effect).

At a step 534, the control element 160 can report its adjusted weights to one or more data repositories 420 or to one or more treatment servers 430. In one embodiment, the control element 160 can report its adjusted weights if they differ substantially from the original weights the control element 160 received.

At a step 535, the receiving data repositories 420 or treatment servers 430 adjust their stored weights in response to the adjustments reported by the control element 160. In one embodiment, the receiving data repositories 420 or treatment servers 430 maintain their stored weights in response to multiple digital eyewear 100 devices; thus, they adjust their stored weights only when adjustments reported by individual control elements 160 are correlated and indicate that their stored weights were not thoroughly accurate.

The method proceeds with the next flow point.

Prevention of Migraines and/or Photophobia

At a flow point 540, the digital eyewear 100 is ready to prevent future migraines.

Similarly, the digital eyewear 100 is ready to prevent future photophobia effects.

At a step 541, the digital eyewear 100 receives time-varying information from the patient sensors 130 and the ambient sensors 140.

At a step 542, the control element 160 predicts whether migraine onset is about to occur near term, or whether a photophobia effect is about to begin near term.

At a step 543, the control element 160 directs the digital eyewear 100, such as the lenses 120, to adjust the augmented reality view to reduce the probability of a future migraine or photophobia effect.

In one embodiment, as described herein, the digital eyewear 100 can be responsive to visual triggers of migraine onset, or beginning of a photophobia effect, such as by canceling those visual triggers in an augmented reality view. For example, the digital eyewear 100 can cancel those visual triggers by shading/inverse-shading of those visual triggers. In such cases, shading/inverse-shading can be performed by one or more of the following:

- LCD elements in the lenses 120, electrically controlled between clear and opaque states;
- for selected frequencies, by antireflective coatings in the lenses 120, or by electrically controlled adaptive antireflective coatings therein;
- for selected frequencies, by electrically controlled e-chromatic elements embedded in the lenses 120;
- for selected frequencies, by electrically controlled micro-mechanical elements (such as MEMS) embedded in the lenses 120;
- for selected frequencies, by electrically controlled elements constructed from one or more of: grapheme, astrophotonics, nanomaterials, electro-nanomaterials, electrophotonics, electropolymers, or other materials.

For another example, the digital eyewear 100 can direct the lenses 120 to adopt a consistent single color, such as red (almost literally "rose colored glasses"), amber, or green; this can have the effect that the patient 170 has, for a selected duration, an augmented reality view that is skewed toward a first set of selected frequencies or away from a second set of selected frequencies For another example, the digital eyewear 100 can replace those visual triggers with other input image elements in the augmented reality view. For another example, the digital eyewear 100 can inject visual calming elements, such as light in the green (520-560 nm) frequency range, which has been found both to reduce the likelihood of migraine onset and to alleviate migraine effects.

For another example, the digital eyewear 100 can direct the lenses 120 to adjust the total light reaching the retina so that the eye operates both its rods and its cones. Rods detect luminance, and operate primarily in relatively dimmer light; when primarily rods are operative, this is called scotopic vision mode ("night vision"), and can include better depth perception. Cones have three types, generally referred to as red, green, and blue, although there is substantial overlap in the sensitivity of different types of cones. Cones operate primarily in relatively brighter light; when primarily cones are operative, this is called photopic mode ("color vision"), and can include better object recognition. A middle range in which both rods and cones are active occurs in relative twilight; this is called mesopic vision mode, which may be an optimum vision mode. It may occur that deliberately causing the patient's eyes to operate in mesopic vision mode can be valuable in preventing or ameliorating migraines.

In one embodiment, as described herein, the digital eyewear 100 can be responsive to audio triggers of migraine onset, such as by canceling those audio triggers in an augmented reality "view". For example, the augmented reality "view" can include sound effects as well as, or in lieu of, light effects. In such cases, the digital eyewear 100 can include earpieces (not shown) that can provide audio inputs to the patient 170. In such cases, the audio inputs can add to or replace external audio inputs. In such cases, the audio inputs can cancel either all frequencies of sound when external audio inputs exceed a selected threshold, can cancel only selected frequencies of sound when those selected frequencies in the external audio inputs, or can add new selected frequencies of sound when audio triggers are determined to raise the likelihood of migraine onset above an acceptable threshold.

After reading this Application, those skilled in the art can see that this can operate similarly to shading/inverse-shading, only as applied to sound in addition to, or instead of, light. Similarly, shading/inverse-shading can be applied to smells, or other senses, in addition to, or instead of, light or sound.

In one embodiment, prevention of migraines or photophobia effects can be particularized to individual patients 170. For example, each patient 170 might have an individual response to light, sound, smell, or other senses. For another example, each patient 170 might have an individual response to their sleep cycle, and thus might have a differential response to time of day and day of the week. For another example, each patient 170 might have an individual response to their menstrual cycle (when they actually have one), and thus might have a differential response to day of the month. For another example, each patient 170 might have an individual response to the ambient environment, as some patients 170 might be more sensitive to weather, to pollutants, or to allergens (and when sensitive to allergens, to different allergens). For another example, each patient 170 might have an individual response to medication, such as prescription medication (e.g., sedatives) or non-prescription medication (e.g., antihistamines).

The method proceeds with the next flow point.

Treatment of Migraines and/or Photophobia

At a flow point 550, the digital eyewear 100 is ready to treat current migraines. Similarly, the digital eyewear 100 is ready to treat currently ongoing photophobia effects.

In one embodiment, the digital eyewear 100 treats current migraines or photophobia effects similarly to preventing future migraines or photophobia effects, with the primary difference being that the control element 160 can be responsive to the patient's actual migraine response or actual photophobia effect, rather to a prediction thereof. For example, the digital eyewear 100 can be disposed to reduce the length or severity of the current migraine or photophobia effect, or to reduce the likelihood of the current migraine or photophobia effect increasing in severity or reaching a dangerous status. In such cases, whether the digital eyewear 100 prefers to reduce the length of the current migraine or photophobia effect, or to reduce its severity, or to reduce the likelihood of an increase in severity, can be responsive to the patient 170, or can be responsive to medical parameters received from data repositories 420 or treatment servers 430, or can be responsive to emergency responders or other medical personnel.

For another example, the digital eyewear 100 can be disposed to cause its communicators 162 to exchange messages with one or more data repositories 420, treatment servers 430, or emergency responders or other medical personnel, with respect to the current migraine or photophobia effect. For another example, as described herein, in the event of a sufficiently severe migraine or photophobia effect, or migraine/photophobia occurring sufficiently severe exogenous conditions (such as when the patient 170 is driving an automobile or operating other heavy machinery), the digital eyewear 100 can be disposed to cause its communicators 162 to request assistance from medical personnel or emergency responders.

Training Self-Care

At a flow point 560, the digital eyewear 100 is ready to train patients to improve their self-care.

As described herein, the patient can engage in actions to reduce the likelihood of migraine onset and to ameliorate a current migraine. Similarly, the patient can engage in actions to reduce the likelihood of beginning of a photophobia effect and to ameliorate an ongoing photophobia effect. The digital eyewear 100 can alert the patient when the likelihood of migraine onset (or beginning of a photophobia effect) exceeds an acceptable threshold, and suggest that the patient 170 take action to alleviate the problem. When the patient 170 does take the suggested action, or any other action with substantial self-care effect, the digital eyewear 100 can provide the patient 170 with positive feedback, hopefully reinforcing patient efforts at self-care.

At a step 561, the digital eyewear 100 receives time-varying information from the patient sensors 130 and the ambient sensors 140.

At a step 562, the control element 160 predicts whether migraine onset (or beginning of a photophobia effect) is about to occur near term.

At a step 563, the control element 160 directs the digital eyewear 100, such as the lenses 120, to adjust the augmented reality view to alert the patient 170 with respect to the likelihood of migraine onset (or beginning of a photophobia effect), and to suggest efforts at self-care.

At a step 564, the control element 160 receives information from the patient sensors 130 indicative of whether the patient 170 has made efforts at self-care.

In one embodiment, the control element 160 can determine whether the likelihood of migraine offset (or beginning of a photophobia effect) has been reduced, and can deem that the patient 170 has made efforts at self-care whenever this is so.

In one embodiment, the control element 160 can adjust the augmented reality view to ask the patient 170 whether they have engaged in the suggested self-care, and can deem that the patient 170 has done so whenever the patient 170 answers affirmatively.

In one embodiment, the control element 160 can determine, in response to the patient sensors 130 and the ambient sensors 140, whether the patient 170 has engaged in the suggested self-care. For example, if the digital eyewear 100 has suggested that the patient 170 dim the lights, the control element 160 can examine the patient sensors 130 to determine if the patient's eyes have been receiving less light, and can examine the ambient sensors 140 to determine if the ambient light level has been reduced. In such cases, the control element 160 can determine whether the patient 170 has engaged in the suggested self-care.

At a step 565, when the control element 160 deems that the patient 170 has engaged in the suggested self-care, the digital eyewear 100 can reinforce the patient's action.

In one embodiment, the control element 160 can adjust the augmented reality view to congratulate the patient 170 for engaging in the suggested self-care. For example, the control element 160 can present a message to the patient 170 saying so. For another example, the control element 160 can gamify the self-care by awarding the patient 170 a selected number of "experience points" for engaging in the suggested self-care. In such cases, medical personnel can optionally reward the patient 170 with extra attention (a congratulatory phone call), with gift cards (insurance companies might find it less expensive to give out a free Big Mac™ than to pay for another doctor visit), with stickers ("I prevented a migraine!"), or with some other positive reinforcement.

The method continues with the next flow point.

End of Method

At a flow point 500B, the method 500 is finished, and ready to be re-performed.

FIG. 6

FIG. 6 shows a conceptual drawing of digital eyewear used with augmented and virtual reality.

The use of the digital eyewear can be described herein with respect to elements shown in the figures, such as:

one or more digital eyewear 100 devices, such as shown in FIGS. 1 and 2;
the patient 170;
a region 610 near the patient 170, lighting/audio sources 611 therein, and objects 612 therein;
an external reality view 620;
one or more augmented reality views 630.

The digital eyewear 100 can be disposed at the patient 170, such as when the digital eyewear includes a headset described with respect to FIG. 1. Alternatively, the digital eyewear 100 can be affixed to or implanted in the patient 170, such as when the digital eyewear 100 includes one or more lenses 120 described with respect to FIG. 2, or such as when the digital eyewear 100 is surgically implanted. As described herein, the patient 170 can have their vision, hearing, or other senses, altered by the digital eyewear 100. As also described herein, the patient 170 can have all or part of the information presented to their vision, hearing, or other senses, replaced by the digital eyewear 100.

Patient Environment

A region 610 near the patient 170 can include one or more lighting/audio sources 611. Lighting sources 611 might include incoming sunlight, light reflected by external objects (such as glare), and light generated or reflected by one or more objects 612. Objects 612 that generate light can include lamps, television screens, computer screens and mobile device screens, and other light-emitters. Objects 612 that reflect light can include glass and shiny surfaces; nearly all objects 612 reject at least some light for at least some frequencies.

Similarly, audio sources 611 might include sound from outside the region, and sound generated by one or more objects 612. Objects 612 that generate sound can include people talking, electronic speakers, household appliances, office equipment; nearly all objects 612 generate at least some sound when they collide with another object. Lighting/audio sources 611 can also include objects that generate signals perceivable by the patient in one or more other senses, including smell, touch, and otherwise.

Other objects 612 can include a second digital eyewear 100, whether currently worn by another patient 170 or otherwise, and one or more communication devices 613, such as a cellular phone or a wi-fi router (such as a device performing an IEEE 802.11 protocol or a variant thereof). The digital eyewear 100 worn by the patient 170 can communicate with the second digital eyewear 100 and with the communication devices 613, as described herein. Similar to the communication links 210 described with respect to FIG. 4, the communication devices 613 can be coupled to a communication network such as the internet.

External Reality

The external reality view 620 can be responsive to a location of the patient 170 in the region 610, to the lighting sources 611, to the objects 612, and possibly to other effects that might affect the patient's senses. Typically, the external reality view 620 includes an element responsive to each individual lighting source 611 and each object 612, such as when a table is illuminated by both incoming sunlight and a computer screen 612c.

The digital eyewear 100 can receive the external reality view 620, such as in response to light input to the lenses 120. The digital eyewear 100 can couple the external reality view 620 to the control element 160. The control element 160 can process all or part of the external reality view 620. The control element 160 can operate as described herein in response thereto, and in response to the patient sensors 130 and the ambient sensors 140, and possibly in response to the patient 170, one or more data repositories 420, and one or more treatment servers 430.

In response to the external reality view 620 (and patient sensors 130, ambient sensors 140, the patient 170, data repositories 420, treatment servers 430), the digital eyewear 100 can monitor and record any "bad" features and any "good" features of those inputs. The "bad" features of those inputs are correlated with increasing the likelihood of, or increasing the severity of, the patient's migraine activity. The "good" features of those inputs are correlated with decreasing the likelihood of, or decreasing the severity of, the patient's migraine activity or photophobia effect. Features can be correlated with migraine onset or "prodome" phase, headache or aura phases, "post-dome" phase, or the absence of migraine activity. Similarly, features can be correlated with stages of a photophobia effect, including a beginning of the effect, an ongoing effect, or a termination of the effect.

In response to bad/good features, the digital eyewear can detect and predict migraines (or photophobia effects), in real-time, as described herein. Similarly, in response thereto, the digital eyewear 100 can also monitor any bad/good features thereof, and record time-series data about them.

Augmented Reality

The digital eyewear 100 can provide an augmented reality view 630 to present to the patient 170 in addition to or in lieu of the external reality view 620. When the digital eyewear 100 determines that some feature of the external reality view 620 is a bad/good feature correlated with increasing/decreasing migraines or photophobia effects, the digital eyewear 100 can remove/reduce bad features, or inject/increase good features, or otherwise provide an augmented reality view 630 with a better feature mix than the external reality view 620. This can have the effect that the patient 170 sees/hears an augmented reality view 630 that is better for them, in that it has lesser likelihood/severity for the patient's migraine activity or photophobia effects.

Treatment Activity

When the patient 170 sees/hears an augmented reality view 630 with that feature removed or mitigated, this can have the effect of helping prevent a patient migraine or photophobia effect. Similarly, when the patient 170 already has a migraine activity or a photophobia effect ongoing, this can have the effect of helping treat the patient migraine activity or photophobia effect.

Similarly, the digital eyewear 100 can determine when that one or more of the treatment devices 150 can help with the patient's migraine activity or photophobia effect, either by improving the bad/good features of the augmented reality view 630, or by otherwise decreasing the likelihood/severity of the patient's migraine activity or photophobia effect. When the digital eyewear 100 determines that the treatment devices 150 can help, it can warn the patient 170, or prompt for consent from the patient 170. Having warned the patient 170, or obtained consent, the digital eyewear 100 can activate the treatment device 150.

To warn or prompt the patient 170, the digital eyewear 100 can inject a message to the patient 170 into the augmented reality view 630. For example, the digital eyewear 100 can inject an image of text into a portion of the augmented reality view 630, such as a corner thereof. To attract the patient's attention, the digital eyewear 100 can cause the text to blink or scroll, or otherwise behave so that the patient 170 adjusts their gaze direction or focus to include the text. The patient 170 can confirm the warning or grant/deny consent by an input to the digital eyewear 100. For example, the patient 170 can conduct an eye action, such as: by a combination of blinking and gaze change activity; by use of a keyboard or touch sensor, including a virtual keyboard or virtual buttons injected into the augmented reality view 630; by moving a finger in a designated area viewable by a camera or motion sensor coupled to the digital eyewear 100, such as a portion of the augmented reality view 630, so that the digital eyewear 100 can identify the motion; by touching a physical contact, such as a button, switch, or capacitive detector; or by otherwise providing an input signal to the digital eyewear 100.

Patient Self-Care

When the bad/good features are within the patient's control, or at least when they are relatively easily so, the digital eyewear 100 can similarly provide an augmented reality view 630 that includes a prompt to the patient 170. The prompt can indicate one or more warnings to the patient 170 of a predicted likelihood/severity of migraine activity or photophobia effects, or can indicate one or more suggestions regarding actions the patient 170 can take to decrease predicted likelihood/severity (herein sometimes called "self-care"). Similarly to the warning or prompt for consent described herein, the warnings or suggestions can be provided to the patient 170 by injecting a message to the patient 170 into the augmented reality view 630. Similarly to the patient 170 granting/denying consent, the patient 170 can inform the digital eyewear 100 whether the patient 170 follows the suggested self-care.

When the digital eyewear 100 provides suggestions regarding self-care actions the patient 170 can take, and the patient 170 does take those actions, the digital eyewear 100 can reward the patient 170. This can help the patient 170 take over a degree of control of migraine activity or photophobia effects, and can help gamify the patient's actions to conduct self-care, as described herein with respect to the step 565.

FIG. 7

FIG. 7 shows a conceptual drawing of a method including using digital eyewear with augmented and virtual reality.

A method 700 includes flow points and method steps as described herein.

Similar to the method 500, although these flow points and method steps are described in a particular order, in the context of the invention there is no particular requirement for any particular order. Also similar to the method 500, one or more portions of the method 700 are sometimes described as being performed by particular elements of the system described with respect to FIG. 1 and FIG. 2, or sometimes by "the method" itself.

The method 700 can perform the functions described with respect to the method 500 in conjunction with flow points and method steps described herein.

Beginning of Method

A flow point 700A indicates a beginning of the method.

The digital eyewear 100 (shown in FIG. 1) performs operations for monitoring, detecting, and predicting migraines, for preventing migraines, for treating migraines, and for training patients to conduct self-care with respect to migraines. Similarly, the digital eyewear 100 performs operations for monitoring, detecting, and predicting photophobia effects, for preventing photophobia effects, for treating photophobia effects, and for training patients to conduct self-care with respect to photophobia effects. These operations can be performed in real-time.

External Reality View

At a flow point 710, the digital eyewear 100 is ready to receive an external reality view 620.

At a step 711, the digital eyewear 100 receives an external reality view 620, including sense inputs such as audio/video and other senses. The external reality view 620 is responsive to the world as it would be perceived by the patient 170 without the digital eyewear 100.

It can occur that the external reality view 620 is relatively static, such as when the patient 170 is sitting in a quiet room at home. Alternatively, it can occur that the external reality view 620 is rapidly changing, such as when the patient 170 is driving an automobile, in which case the external reality view 620 can include a view through the windshield.

As described herein, the external reality view 620 can include, or the control system 160 can determine in response thereto, one or more factors that can be correlated with migraine onset or migraine activity. Similarly, the control system 160 can determine in response thereto, one or more factors that can be correlated with photophobia effects. These factors can include:

visual input or light intensity; such as sudden glare, rapidly flashing bright light, lighting that changes with unstable frequency;

total light intensity, total light intensity in the blue (approximately 450-490 nm) and ultraviolet (approximately <300 nm) frequency ranges, to total light intensity applied to selected regions of the retina (such as those portions of the retina including the cone receptors or the rod receptors), at least first and second time-derivatives thereof, at least first and second statistical moments thereof, frequency of modulation, stability of frequency of modulation;

light intensity in selected frequency bands, such as blue and ultraviolet, total light intensity actually applied to specific portions of the retina, such as only rods or only cones;

light intensity from selected directions, such as peripheral vision, including side to side and up/down peripheral vision;

pupillary diameter, at least first and second time-derivatives thereof, at least first and second statistical moments thereof, frequency of modulation thereof, and match between right and left eye thereof;

complexity of an input image, or a rapidity or complexity with which the input image changes;

sound intensity, at least first and second time-derivatives thereof, at least first and second statistical moments thereof, frequency of modulation thereof, match between right and left ear thereof, discordancy thereof;

sound intensity in selected frequency bands, at least first and second time-derivatives thereof, at least first and second statistical moments thereof, frequency of modulation thereof, match between right and left ear thereof, discordancy thereof, and unusual time intervals thereof;

patient response to sensory inputs increasing in intensity or discordancy/complexity.

The method continues with the next flow point.

Correlate Features

At a flow point 720, the digital eyewear 100 is ready to correlate features with patient migraine activity or photophobia effects.

At a step 721, the digital eyewear 100 can receive patient reports of migraine onset or migraine activity, or photophobia effects.

As described herein, the digital eyewear's control system 160 can determine one or more factors that can be correlated with migraine onset or migraine activity, or photophobia effects. For example, patient reports can be used as an indicator of migraine activity or photophobia effects. Patient reports can be received using steps described with respect to the flow point 740.

At a step 722, the digital eyewear 100 can determine factors that are correlated with migraine onset or migraine activity, or photophobia effects. As part of this step, for example, the digital eyewear 100 can use techniques described with respect to the step 533, such as adaptive sensors and machine learning.

The method continues with the next flow point.

Augmented Reality View

At a flow point 730, the digital eyewear 100 is ready to present an augmented reality view 630.

At a step 731, the digital eyewear 100 determines an adjustment to the external reality view 620 desired to decrease the likelihood/severity of a patient migraine or a photophobia effect.

At a step 732, the digital eyewear 100 adjusts the external reality view 620 by decreasing bad factors or increasing good factors. As part of this step, decreasing bad factors can include shading/inverse-shading them so that they have less intensity. As part of this step, increasing good factors can include shading/inverse-shading them so that they have greater intensity, and can include injecting them so they have greater intensity.

For example, as described herein, shading/inverse-shading can be performed by adjusting the lenses response to color or to monochrome light intensity. The shading/inverse-shading can be performed with respect to particular frequencies, such as blue light or ultraviolet light. The shading/inverse-shading can also be performed with respect to particular directions from which the light is infalling, such as light directed at areas of the patient's retina, at the patient's rods/codes, or the patient's peripheral vision.

For another example, the digital eyewear 100 can inject visual calming elements, such as light in the green (approximately 520-560 nm) frequency range.

For another example, the digital eyewear 100 can adjust the total light reaching the retina so that the eye operates in a mesopic vision mode.

For another example, the digital eyewear 100 can adjust the total sound reaching the patient's ears, or can adjust sound in selected frequency bands, or can inject sound in selected frequency bands.

The method continues with the next flow point.

Communicate with Patient

At a flow point 740, the digital eyewear 100 is ready to exchange one or more messages to the patient 170, using the augmented reality view 630.

At a step 741, the digital eyewear 100 can receive one or more messages from the patient 170, such as detecting patient actions, such as one or more of:

pressing, touching, or bringing a body part (such as a finger) near, an input device;

moving a body part (such as a hand or finger) in a camera view of the digital eyewear 100, such as typing on a virtual keyboard presented in the augmented reality view 630, gestures by a hand or other body part;

receiving a message (such as a SMS or MMS message, a wi-fi packet, an internet packet, an email message) from a mobile device, such as a smartphone;

eye blinks, eye gaze, eye gaze change (such as eye gaze change from right to left, left to right, up to down, down to up), eye focus change (such as distant to near, near to distant), or combinations thereof;

voice commands by the patient 170.

As described herein, patient input can be patient-initiated or can be in response to a request from the digital eyewear 100.

At a step 742, the digital eyewear 100 can send one or more messages to the patient, such as injecting the message into the augmented reality view 630. The digital eyewear 100 can inject messages into the augmented reality view 630 by shading/inverse-shading one or more pixels in the field of view in the augmented reality view 630, such as:

shading/inverse-shading pixels in the augmented reality view 630 to form text, emoticons, other icons, other pictures;

moving a text or picture message so that it is within gaze direction and focus for the patient 170;

adjusting a text or picture message so that it attracts attention, such as by blinking, scrolling, or otherwise;

injecting bells, whistles, buzzers, or other sounds into the audio presented to the patient 170;

injecting voice messages into the audio presented to the patient 170;

injecting other sensory inputs to the patient 170, such as haptic inputs (vibration or otherwise), electrical stimulation, smell, water mist (such as applied to the eyes), or otherwise.

The digital eyewear 100 can repeat the steps 741 and 742 until the control element 160 determines that sufficient information has been exchanged with the patient 170.

End of Method

At a flow point 700B, the method 700 is finished, and ready to be re-performed.

Alternative Embodiments

After reading this application, those skilled in the art would recognize that techniques shown in this application are applicable to more than just the specific embodiments shown herein. For example, the concept of care and prevention, as described herein with respect to migraines, is intended to be broad. It can easily be extended to other types of chronic or recurrent concerns, including stress headaches, gastroenterological reflux (GERD), psychological anxiety, and other medical and non-medical conditions.

While multiple embodiments are disclosed, including variations thereof, still other embodiments will become apparent to those skilled in the art from the enclosed detailed description, which shows and describes illustrative embodiments, which are capable of modifications in various aspects, all without departing from their scope or spirit. The drawings and detailed description are illustrative in nature and not restrictive. The claims are hereby incorporated by reference.

The invention claimed is:

1. Digital eyewear, including
an interface between an ambient environment and a patient sensory organ;
wherein, responsive to biometric monitoring measurements, the digital eyewear performs procedures for migraine, photophobia, or neuro-ophthalmic disorder; the procedures including one or more of: monitoring, diagnosing, detection, prediction, prevention, measurement, treatment, amelioration, or training self-care;
wherein the biometric monitoring measurements include, with respect to a particular individual patient or a selected collection of patients, information about onset or progress of migraine, photophobia, or neuro-ophthalmic disorder; information about a history of migraine, photophobia, or neuro-ophthalmic disorder; information from patient sensors or ambient sensors;
the digital eyewear being disposed, in response thereto, to present one or more augmented reality views, to present one or more sensory inputs, to alter one or more aspects of an ambient environment, or to reward patient self-care with respect to one or more of migraines, photophobia, or neuro-ophthalmic disorder.

2. Digital eyewear as in claim 1,
including a communication element disposed to couple information with respect to one or more of: a current or near-term likelihood or severity of events associated with migraine, photophobia, or neuro-ophthalmic disorder; onset or progress of events associated with migraine, photophobia, or neuro-ophthalmic disorder;
to one or more of: medical personnel or emergency personnel, a second digital eyewear, or the patient associated with possible migraine, photophobia, or neuro-ophthalmic disorder.

3. Digital eyewear as in claim 2,
wherein communicating with the patient includes one or more of:
warning of one or more of: a current or near-term likelihood or severity of events associated with migraine, photophobia, or neuro-ophthalmic disorder; onset or progress of events associated with migraine, photophobia, or neuro-ophthalmic disorder;
suggesting or rewarding self-care with respect to one or more of: a current or near-term likelihood or severity of events associated with migraine, photophobia, or neuro-ophthalmic disorder; onset or progress of events associated with migraine, photophobia, or neuro-ophthalmic disorder;
suggesting or rewarding disengaging from activity that would be dangerous when associated with events associated with migraine, photophobia, or neuro-ophthalmic disorder.

4. Digital eyewear as in claim 3,
wherein the suggested or rewarded self-care includes one or more of:
disengaging from driving or operating heavy machinery;
disengaging from an emotional situation; relaxing, engaging in meditation, or taking a nap; or contacting a support person;
disengaging from viewing a first selected audio/visual image, or engaging in viewing a second selected audio/visual image;
engaging in viewing a selected augmented reality view; or using medication, or contacting medical personnel or emergency personnel.

5. Digital eyewear as in claim 1,
including a computing element disposed to determine, in response to the monitoring measurements, with respect to one or more of: a selected particular patient, a selected collection of patients, a current or near-term likelihood of occurrence or severity of effects with respect to migraine, photophobia, or neuro-ophthalmic disorder.

6. Digital eyewear as in claim 1,
including a computing element disposed to determine, in response to the monitoring measurements, with respect to one or more of: a selected particular patient, a selected collection of patients, one or more correlations between inputs associated with monitoring, diagnosing, detection, prediction, prevention, measurement, treatment, amelioration, or training self-care; with respect to effects associated with migraine, photophobia, or neuro-ophthalmic disorder.

7. Digital eyewear as in claim 1,
wherein one or more of: the information about progress of migraine, photophobia, or neuro-ophthalmic disorder; the information about a history of migraine, photophobia, or neuro-ophthalmic disorder;
is with respect to one or more of: a selected particular patient, a selected collection of patients.

8. Digital eyewear as in claim 1,
wherein operating the interface is performed in response to one or more of: a second digital eyewear, a remote database.

9. Digital eyewear as in claim 8,
wherein the remote database includes information with respect to one or more of: medical information with respect to migraine, photophobia, or neuro-ophthalmic disorder; medical information with respect to particular patients.

10. Digital eyewear as in claim 1,
wherein presenting one or more augmented reality views, presenting one or more sensory inputs, altering one or more aspects of an ambient environment, or rewarding patient self-care
include an operation with respect to the interface.

11. Digital eyewear as in claim 1,
wherein presenting one or more augmented reality views, presenting one or more sensory inputs, altering one or more aspects of an ambient environment, or rewarding patient self-care
is performed in real time with respect to one or more of: an external sensory input, a patient migraine effect, a patient photophobia effect, or a patient neuro-ophthalmic disorder.

12. Digital eyewear as in claim 1,
wherein presenting one or more augmented reality views, presenting one or more sensory inputs, altering one or more aspects of an ambient environment, or rewarding patient self-care is utilized to adjust a sensory input to a patient;
wherein the adjusted sensory input is less likely than the unadjusted sensory input to induce or maintain a patient migraine effect, a patient photophobia effect, or a patient neuro-ophthalmic disorder.

13. Digital eyewear as in claim 1,
wherein presenting one or more augmented reality views, presenting one or more sensory inputs, altering one or more aspects of an ambient environment, or rewarding patient self-care is utilized with respect to one or more of: an ambient environment effect, an ameliorative treatment, a desired audio or visual frequency, an external device display, an informational message, a light or sound intensity, a light or sound intensity within a selected range of frequencies, a measure of perceptual noise, a surface having glare or a measure of glare, or an ultraviolet source or a measure of incoming ultraviolet light.

14. Digital eyewear as in claim 1,
wherein presenting one or more augmented reality views includes one or more of:
reducing a light or sound intensity of the augmented reality views;
increasing a light or sound intensity of the augmented reality views in a desired frequency range; or
reducing complexity of, reducing activity in, reducing transitions or flashing in, reducing a measure of glare in, or increasing calming elements in, the augmented reality views;
with respect to one or more of: the entire augmented reality views, a selected frequency range of the augmented reality views, a selected portion of the augmented reality views.

15. Digital eyewear as in claim 1,
wherein the interface includes one or more of: an audio filter, an audio or visual input element, or a lens or a visual filter.

16. Digital eyewear as in claim 15,
wherein the audio filter or the visual filter affects one or more of: an audio or visual intensity in a selected frequency range, a total audio or visual intensity, an entire audio or visual input to a patient, a selected portion of the audio or visual input to the patient.

17. Digital eyewear as in claim 15,
wherein the interface includes
a first part disposed to receive input from an external environment;
a second part disposed to present input to a patient.

18. Digital eyewear as in claim 15,
wherein the interface includes
one or more of: a contact lens, a wearable or implantable lens, a retinal image display, an optic nerve stimulator, an earphone.

19. Digital eyewear as in claim 15,
wherein the interface is disposed to be mounted on a wearable element.

20. Digital eyewear, including
one or more biometric sensors, patient sensors, or ambient sensors;
a presentation element disposed to conduct, with respect to a particular individual patient, one or more of: presenting or altering one or more of: augmented reality views, external sensory inputs, or aspects of an ambient environment;
wherein operation of the presentation element includes one or more of: monitoring, diagnosing, detection, prediction, prevention, measurement, treatment, amelioration, or training self-care;
the digital eyewear being disposed, in response to the one or more biometric sensors, patient sensors, or ambient sensors; with respect to the particular individual patient or a selected collection of patients; to conduct, with respect to migraine, photophobia, or neuro-ophthalmic disorder; one or more of:
operating the presentation element; or
maintaining information, with respect to a particular individual patient or a selected collection of patients, about one or more of: current or near-term likelihood of occurrence or severity of migraine, photophobia, or neuro-ophthalmic disorder; onset or progress of events associated with migraine, photophobia, or neuro-ophthalmic disorder; or history of or occurrence or severity of migraine, photophobia, or neuro-ophthalmic disorder;
wherein the digital eyewear, in response to the one or more biometric sensors, patient sensors, or ambient sensors, is disposed to determine one or more correlations with respect to migraine, photophobia, or neuro-ophthalmic disorder; or between inputs associated therewith.

21. Digital eyewear as in claim 20,
including a communication element disposed to couple to one or more of: medical or emergency personnel, a remote database or server, or a second digital eyewear.

22. Digital eyewear as in claim 21,
wherein operation of the communication element includes one or more of:
communicating with the medical or emergency personnel with respect to a patient migraine effect, a patient photophobia effect, or a patient neuro-ophthalmic disorder;
communicating with the remote database or server with respect to information associated with a patient migraine effect, a patient photophobia effect, or a patient neuro-ophthalmic disorder; or
communicating with the second digital eyewear with respect to assisting the patient with a patient migraine effect, a patient photophobia effect, or a patient neuro-ophthalmic disorder.

23. Digital eyewear as in claim 20,
including a computing element disposed to determine, in response to the monitoring measurements,
with respect to one or more of: a selected particular patient, a selected collection of patients, one or more correlations between inputs associated with monitoring, diagnosing, detection, prediction, prevention, measurement, treatment, amelioration, or training self-care;
with respect to effects associated with migraine, photophobia, or neuro-ophthalmic disorder.

24. Digital eyewear as in claim 20,
including a memory disposed to maintain information, with respect to a particular individual patient or a selected collection of patients, about one or more of: current or near-term likelihood of occurrence or severity of migraine, photophobia, or neuro-ophthalmic disorder; onset or progress of events associated with migraine, photophobia, or neuro-ophthalmic disorder; or history of or occurrence or severity of migraine, photophobia, or neuro-ophthalmic disorder;
wherein the digital eyewear, in response to the one or more biometric sensors, patient sensors, or ambient sensors, is disposed to determine one or more correlations with respect to migraine, photophobia, or neuro-ophthalmic disorder; or between inputs associated therewith.

25. Digital eyewear as in claim 24,
including a computing element disposed to adjust or replace information maintained by a memory in response to one or more of:
current occurrence or severity of migraine, photophobia, or neuro-ophthalmic disorder;

onset or progress of events associated with migraine, photophobia, or neuro-ophthalmic disorder; or history of or occurrence or severity of migraine, photophobia, or neuro-ophthalmic disorder.

26. Digital eyewear as in claim 20, wherein the ambient sensors include one or more of:

a light spectrum sensor, a light intensity sensor, a polarization sensor, a weather measurement sensor, an irritant measurement sensor, a location sensor, a location sensor, a movement sensor.

27. Digital eyewear as in claim 20, wherein the biometric sensors include one or more of:

a pupillometry sensor, a gaze detection sensor, a blink rate sensor, an electroencephalography sensor, an electromyography sensor, an electrocardiography sensor, an accelerometer, a galvanometer, an oxymeter sensor, a microphone, a camera, an intake/outgo sensor, a sleep sensor, a menstrual sensor.

28. Digital eyewear as in claim 20, wherein the presentation element includes one or more of:

an audio or video shading/inverse-shading element, a polarization element, a lighting or glare protection element, an light or sound injection element, a frequency conversion element, a medication element, a moisturizer element, a transcutaneous supraorbital stimulation ("t-SNS") element.

29. Digital eyewear as in claim 20, wherein operation of the presentation element includes one or more of:

one or more of: adjusting or replacing, a light or sound intensity of the augmented reality views, with respect to at least a selected frequency range, and with respect to at least a selected part of the sensory input; or presenting a message to the patient.

30. Digital eyewear as in claim 20, wherein the presentation element includes an interface between an ambient environment and a patient sensory organ;

the presentation element being disposed, with respect to a sensory input from the ambient environment, to adjust or replace the sensory input with respect to the patient sensory organ;

wherein the patient sensory organ includes one or more of: an eye, an ear, nose, skin, a nerve signal.

* * * * *